US012709602B2

(12) United States Patent
Sun et al.

(10) Patent No.: US 12,709,602 B2
(45) Date of Patent: Aug. 18, 2026

(54) INTERMEDIATES FOR MAKING DERIVATIVES OF SUBSTITUTED MORPHOLINES

(71) Applicant: Supernus Pharmaceuticals, Inc., Rockville, MD (US)

(72) Inventors: Yanjun Sun, Kendall Park, NJ (US); Bhaskara Rao Nallaganchu, Hillsborough, NJ (US); Gary L. Olson, Mountainside, NJ (US)

(73) Assignee: Supernus Pharmaceuticals, Inc., Rockville, MD (US)

( * ) Notice: Subject to any disclaimer, the term of this patent is extended or adjusted under 35 U.S.C. 154(b) by 104 days.

(21) Appl. No.: 18/123,102

(22) Filed: Mar. 17, 2023

(65) Prior Publication Data

US 2023/0295100 A1 Sep. 21, 2023

Related U.S. Application Data

(60) Provisional application No. 63/321,423, filed on Mar. 18, 2022.

(51) Int. Cl.
*C07D 265/30* (2006.01)
*B01J 31/02* (2006.01)

(52) U.S. Cl.
CPC ........ *C07D 265/30* (2013.01); *B01J 31/0239* (2013.01); *B01J 2231/347* (2013.01); *B01J 2231/348* (2013.01); *B01J 2531/002* (2013.01); *C07B 2200/07* (2013.01)

(58) Field of Classification Search
CPC ................ C07D 265/30; B01J 31/0239; B01J 2231/347; B01J 2231/348; B01J 2531/002; C07B 2200/07
See application file for complete search history.

(56) References Cited

U.S. PATENT DOCUMENTS

| | | | | |
|---|---|---|---|---|
| 3,857,839 | A * | 12/1974 | Lee | C07D 265/30 544/158 |
| 4,229,449 | A | 10/1980 | Melloni | |
| 5,559,111 | A | 9/1996 | Goschke et al. | |
| 6,313,308 | B1 | 11/2001 | Singh et al. | |
| 6,376,711 | B1 | 4/2002 | Henegar et al. | |
| 6,506,750 | B1 | 1/2003 | Ducoux et al. | |
| 7,501,414 | B2 | 3/2009 | Tornoe et al. | |
| 7,659,394 | B2 | 2/2010 | Barta et al. | |
| 7,994,315 | B2 | 8/2011 | Okuyama et al. | |
| 9,403,783 | B2 * | 8/2016 | Liang | C07D 265/30 |
| 10,337,039 | B2 | 7/2019 | Trussardi et al. | |
| 11,634,415 | B2 | 4/2023 | Padia | |
| 11,964,951 | B2 * | 4/2024 | Sun | B01J 31/0239 |
| 2011/0251198 | A1 * | 10/2011 | Liang | A61P 25/24 544/170 |
| 2022/0306618 | A1 | 9/2022 | Padia | |

FOREIGN PATENT DOCUMENTS

| | | | |
|---|---|---|---|
| CA | 2356299 A1 | 8/2000 | |
| EP | 0 521 827 A1 | 1/1993 | |
| GB | 1 260 886 A | 1/1972 | |
| WO | WO-2022/198062 A2 | 9/2022 | |

OTHER PUBLICATIONS

U.S. Appl. No. 63/162,671, filed Mar. 18, 2021, Padia, Janak Khimchand.
Howe et al., "Optical Isomers of 2-(2-Ethoxyphenoxymethyl-tetrahydro-1,4-oxazine (Viloxazine) and Related Compounds," Journal of Medicinal Chemistry, Jan. 9, 1976, 19(8):1074-1076.
Yang et al., "Enzyme-mediated hydrolytic activation of prodrugs, Acta Pharmaceutica Sinica B," 2011, 1(3):143-159.
Audouze et al., "New Series of Morpholine and 1,4-Oxazepane Derivatives as Dopamine D 4 Receptor Ligands: Synthesis and 3D-QSAR Model," J. Med. Chem., 2004, 47(12):3089-3104, American Chemical Society, XP002430838.
Boot et al., "Discovery and structure-activity relationships of novel selective norepinephrine and dual serotonin/norepinephrine reuptake inhibitors," Bioorganic & Medicinal Chemistry Letters, Feb. 1, 2005, 15(3):699-703.

(Continued)

*Primary Examiner* — Amy L Clark
*Assistant Examiner* — Jalisa Holmes Ferguson
(74) *Attorney, Agent, or Firm* — Foley & Lardner LLP

(57) ABSTRACT

Provided here are methods of making derivatives and prodrugs of substituted morpholines or pharmaceutically acceptable salts thereof. Further provided are methods of making derivatives and prodrugs of substituted morpholines having the following chemical structure:

(IIf)

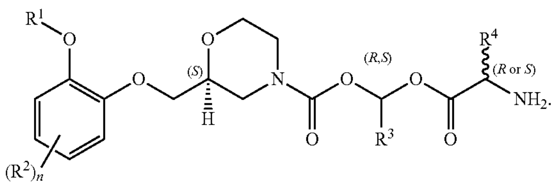

6 Claims, 7 Drawing Sheets

(56) References Cited

OTHER PUBLICATIONS

Henegar, Kevin E., "Concise Synthesis of (S)-N-BOC-2-Hydroxymethylmorpholine and (S)-N-BOC-Morpholine-2-carboxylic Acid," The Journal of Organic Chemistry, May 2008, 73(9):3662-3665.
International Search Report and Written Opinion dated Jul. 21, 2023 in PCT/US2023/015461.
Letavic et al., "2-Aryloxymethylmorpholine histamine H"3 antagonists," Bioorganic & Medicinal Chemistry Letters, Nov. 1, 2008, 18(21):5796-5799.
Dorwald, F. Zaragoza, Side Reactions in Organic Synthesis, 2005, Wiley: VCH Weinheim Preface, pp. 1-16, 40-41 & Chapter 8, pp. 279-309 (37 pages total).
Metro et al., "Syntheses of (S,S)-Reboxetine via a Catalytic Stereospecific Rearrangement of Beta-Amino Alcohols," The Journal of Organic Chemistry, Dec. 20, 2007, 73(2):707-710.
Aparicio et al., "Application of amide-stabilized sulfur ylide reactivity to the stereodivergent synthesis of (R, S)-and (S, R)-reboxetine," Tetrahedron: Asymmetry, 2009, 20(23):2764-2768.
Balsamo et al., "3-[(2-Ethoxyphenoxy) methyl] piperidine derivatives. Synthesis and Antidepressant Activity," Journal of Medicinal Chemistry, 1987, 30(1):222-225.
Breuning et al., "Efficient One-Pot Synthesis of Enantiomerically Pure 2-(Hydroxymethyl) morpholines," European Journal of Organic Chemistry, 2007, 13:2100-2106.
Ghosh et al., "Lewis acid mediated intramolecular C—O bond formation of alkanol-epoxide leading to substituted morpholine and 1,4-oxazepane derivatives: total synthesis of (±)-Viloxazine," Tetrahedron, 2016 (online Dec. 10, 2015), 72(5):690-698.
Lin et al.,. "Synthesis, enantiomeric resolution, F-18 labeling and biodistribution of reboxetine analogs: promising radioligands for imaging the norepinephrine transporter with positron emission tomography," Nuclear Medicine and Biology, 2005, 32(4):415-422.
Lin et al., "Synthesis, enantiomeric resolution, and selective C-11 methylation of a highly selective radioligand for imaging the norepinephrine transporter with positron emission tomography," Chirality, Aug. 2004, 16(7):475-481.
Prabhakaran et al., "Chiral synthesis of (2S, 3S)-2-(2-morpholin-2-yl-2-phenylmethoxy) phenol," Chirality, Mar. 2004, 16(3):168-173.
Steiner, Melanie, Chiral 9-Oxabispidine Design, enantioselective representation and Application in asymmetric synthesis, Doctoral dissertation, Universität Würzburg, URL: http://d-nb.info/1008731544/34, 2010, 189 pages, with English machine translation 189 pages.
Yu et al., "The synthesis of (R, S)-reboxetine employing a tandem cyclic sulfate rearrangement—opening process," Tetrahedron: Asymmetry, 2012, 23(9):650-654.
Zeng et al., "Synthesis, in vitro characterization, and radiolabeling of reboxetine analogs as potential PET radioligands for imaging the norepinephrine transporter," Bioorganic & Medicinal Chemistry, 2008, 16(2):783-793.
Gajare et al., "A short diastereoselective synthesis of cis-(2S,4S) and cis-(2R,4R)-4-hydroxyprolines," Tetrahedron Letters, 2015, 56:3743-3746.
Olofson et al., "A new reagent for the selective, high-yield N-dealkylation of tertiary amines: improved syntheses of naltrexone and nalbuphine," J. Org. Chem., Jun. 1, 1984, 49(11):2081-2082.
Pelander et al., "Preparation of N-demethylated drug metabolites for analytical purposes using 1-chloroethyl chloroformate," Forensic Science International, Mar. 14, 1997, 85(3):193-198.
Son et al., "Dynamic Kinetic Resolution-Based Asymmetric Transfer Hydrogenation of 2-Benzoylmorpholinones and Its Use in Concise Stereoselective Synthesis of All Four Stereoisomers of the Antidepressant Reboxetine," The Journal of Organic Chemistry, 2013, 78:8396-8404.

* cited by examiner

INTERMEDIATES FOR MAKING DERIVATIVES OF SUBSTITUTED MORPHOLINES

CROSS-REFERENCE TO RELATED APPLICATIONS

This application claims priority to U.S. Provisional Application No. 63/321,423, filed Mar. 18, 2022, the entire contents of which are incorporated herein by reference.

FIELD

Described herein are methods for making derivatives and prodrugs of substituted morpholines or pharmaceutically acceptable salts thereof.

BACKGROUND

The compound 2-((2-ethoxyphenoxy)methyl)morpholine is known to have several desirable pharmacologic uses, including treatment of depression, nocturnal enuresis, narcolepsy, sleep disorders, and alcoholism, among others. 2-((2-ethoxyphenoxy)methyl)morpholine was previously marketed in several European countries for the treatment of major depressive disorder (MDD). It is an inhibitor of the reuptake of norepinephrine ("NRI"), but may also enhance the release of serotonin from neuronal stores. However, treatment with 2-((2-ethoxyphenoxy)methyl)morpholine has been associated with numerous side effects including nausea, vomiting, loss of appetite, increased erythrocyte sedimentation, EKG and EEG anomalies, epigastric pain, diarrhea, constipation, vertigo, orthostatic hypotension, edema of the lower extremities, dysarthria, tremor, psychomotor agitation, mental confusion, inappropriate secretion of antidiuretic hormone, increased transaminases, and seizure.

2-((2-ethoxyphenoxy)methyl)morpholine is a chiral molecule whose desired biological properties are associated with the (S)-enantiomer, which is known to exhibit five times the pharmacological activity as compared to the (R)-(+)-isomer. See, e.g., "Optical Isomers of 2-(2-ethoxyphenoxymethyl)tetrahydro-1,4 oxazine (viloxazine) and Related Compounds" (Journal of Medicinal Chemistry, Jan. 9, 1976, 19(8); 1074) in which it is disclosed that optical isomers of 2-(2-ethoxyphenoxymethyl)tetrahydro-1,4-oxazine and 2-(3-methoxyphenoxymethyl)tetrahydro-1,4-oxazine were prepared and absolute configurations assigned. The synthesis of optical isomers of viloxazine analogs of known configuration was accomplished by resolution of the intermediate 4-benzyl-2-(p-toluenesulfonyloxymethyl)tetrahydro-1,4-oxazine isomers.

In order to minimize the side effects associated with 2-((2-ethoxyphenoxy)methyl)morpholine, chemists have synthesized derivatives, prodrugs, and analogs that retain the pharmacologic properties of 2-((2-ethoxyphenoxy)methyl)morpholine, as shown in U.S. application Ser. No. 63/162,671, the entire contents of which are incorporated herein. Prodrugs are a class of derivatives that in many instances have little or no pharmacological activity, which are converted in vivo to therapeutically active compounds. In some instances, the prodrug itself may possess biological activity. Prodrug activation may occur by enzymatic or non-enzymatic cleavage of the temporary bond between the carrier and the drug molecule, or a sequential or simultaneous combination of both. Additional methods for synthesizing prodrugs of 2-((2-ethoxyphenoxy)methyl)morpholine would be beneficial.

Prodrugs may provide compounds with superior physicochemical properties as compared to the parent molecule, which may overcome barriers for absorption, distribution, metabolism, excretion, and toxicity (ADMET). These prodrugs may show improved absorption, solubility, permeability, stability, and pharmacokinetic performance. The prodrug may exhibit a longer half-life as compared to the parent molecule. Prodrugs may be prepared by coupling of the parent drug at reactive sites with prodrug moieties that modify the parent drug and are convertible from the prodrug to the parent drug by enzymatic or non-enzymatic processes. The reactive sites on the drug may include, but are not limited to, hydroxyl, carboxyl, amino, heteroamino, thiol, amide, and related reactive groups. These are coupled to form prodrugs with alkyl, aralkyl, acyl, carbamoyl, acyloxy, and moieties that have combined groups such as diacylacetals or acylhydroxyalkyl, groups. Other examples are described in the literature (see Yang, Liu, et al., Acta Pharmaceutica Sinica B 2011: 1(3), 143-159 and references described therein).

The newly synthesized 2-((2-ethoxyphenoxy)methyl) morpholine analogs, prodrugs, enantiomers, and derivatives, with the derivatization of the amine group of the morpholine in the structure of 2-((2-ethoxyphenoxy)methyl)morpholine produce chemically stable compounds to serve as novel compounds and intermediates. These 2-((2-ethoxyphenoxy) methyl)morpholine analogs, enantiomers, prodrugs, and derivatives, can be used in pharmaceutical compositions and for the treatment of central nervous system (CNS) disorders or as intermediates in their preparation.

Previously disclosed syntheses of these 2-((2-ethoxyphenoxy)methyl)morpholine analogs, prodrugs, and derivatives, suffer from a number of deficiencies, such as low reaction yield, reaction byproducts, difficult separation of enantiomers and impurities in the resulting product. Effective elimination or removal of impurities, especially those impurities possessing genotoxicity or other toxicities, is critical to render safe pharmaceutical products. Disclosed herein are solutions to these and other related problems.

The preparation of the (S)-enantiomer of the 2-((2-ethoxyphenoxy)-methyl)morpholine analogs, prodrugs, and derivatives by a route that does not require a resolution of a precursor is also desirable and a solution to this issue is provided by the processes described herein.

SUMMARY OF THE INVENTION

Provided herein are new and improved methods of manufacture of morpholine derivatives and their various salts, as well as methods of manufacture of novel intermediate reaction products. Further provided are methods for synthesis and identification and characterization of novel intermediates of the morpholine derivatives.

In one aspect, the invention provides a method of manufacturing a morpholine derivative of formula (IIb):

(IIb)

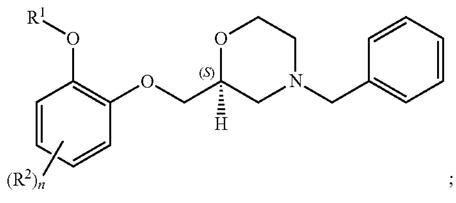

;

or a pharmaceutically acceptable salt thereof, the method comprising:

(a) reacting a compound of formula

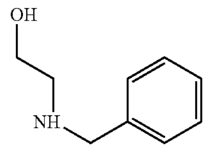 [SMILES: OCCNCc1ccccc1]

with (S)-(+)-epichlorohydrin to form a chlorohydrin compound of formula

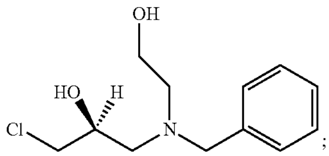 [SMILES: OCCN(Cc1ccccc1)C[C@H](O)CCl]
;

(b) contacting the chlorohydrin compound with a base and phase transfer catalyst to form an epoxide compound of formula

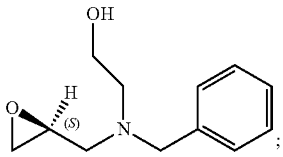
;

(c) contacting the epoxide compound with a base and a compound of formula:

(Ia)

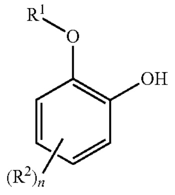

to form a diol compound of formula (IIa)

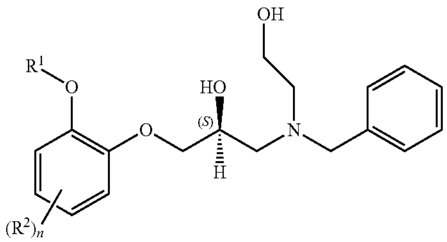
;

(d) contacting the diol compound with a base followed by addition of a sulfonyl halide to form an intermediate sulfonate of formula (IIa')

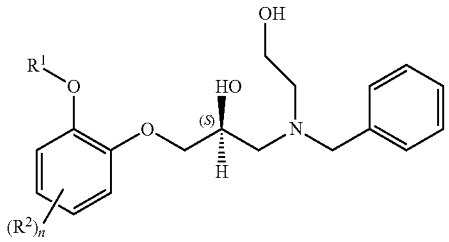
, wherein Z is a sulfonyl leaving group, that cyclizes in situ to give an N-benzyl protected morpholine compound of formula (IIb)

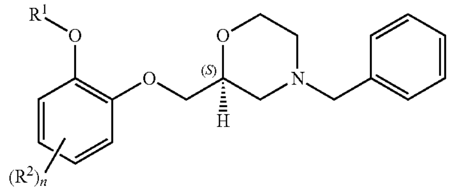
;

and (e) forming the HCl salt of the compound of formula IIb and recrystallizing it to afford the highly pure (S)-enantiomer as an HCl salt;

wherein $R^1$ is $C_1$-$C_6$ alkyl, aryl, heteroaryl, or heterocycloalkyl; and each $R^2$ is independently selected from F, Cl, Br, I, CN, $NO_2$, $C_1$-$C_6$ alkyl, aryl, heteroaryl, or heterocycloalkyl; and n is 0, 1, 2, 3, or 4.

In an embodiment, the invention provides a method of manufacturing a morpholine derivative of formula (IIb):

(IIb)

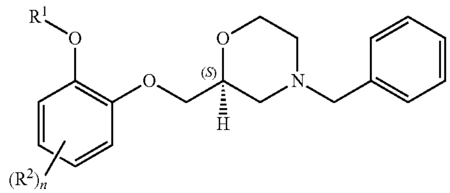
;

or a pharmaceutically acceptable salt thereof, the method comprising:

(a) reacting a compound of formula

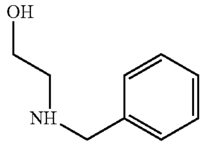 [SMILES: OCCNCc1ccccc1]

with (S)-(+)-epichlorohydrin to form a chlorohydrin compound of formula

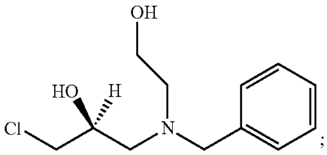 [SMILES: OCCN(Cc1ccccc1)C[C@H](O)CCl]
;

(b) contacting the chlorohydrin compound with a base and phase transfer catalyst to form an epoxide compound of formula

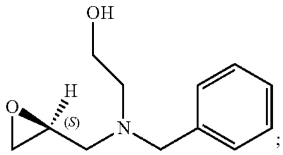
;

(c) contacting the epoxide compound with a base and a compound of formula:

(Ia)

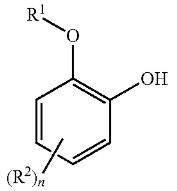

to form a diol compound of formula (IIa)

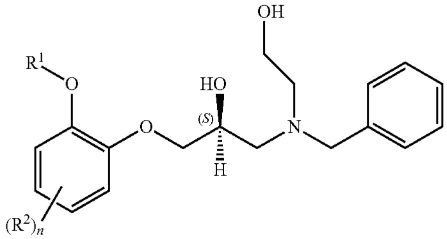
;

(d) contacting the diol compound with a base followed by addition of a sulfonyl halide to form an intermediate sulfonate of formula (IIa')

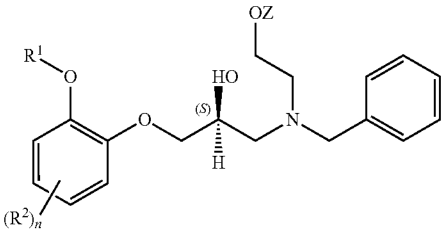
, wherein Z is a sulfonyl leaving group, that cyclizes in situ to give an N-benzyl protected morpholine compound of formula (IIb)

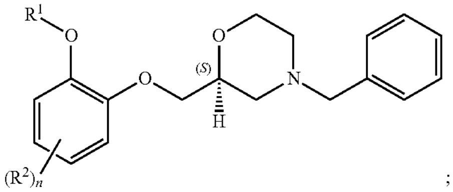
;

and (e) forming the HCl salt of the compound of formula IIb and recrystallizing it to afford the highly pure (S)-enantiomer as an HCl salt;

wherein $R^1$ is $C_1$-$C_6$ alkyl, aryl, or heteroaryl; and each $R^2$ is independently selected from F, Cl, Br, I, CN, $C_1$-$C_6$ alkyl, aryl, or heteroaryl; and n is 0, 1, 2, 3, or 4.

In another aspect, the invention provides a method of manufacturing a morpholine derivative of formula (IIe):

(IIe)

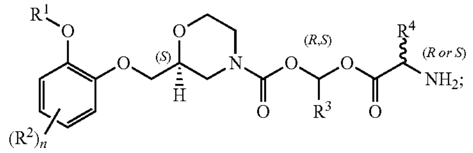

or a prodrug or a pharmaceutically acceptable salt thereof, the method comprising:

(a) reacting a compound of formula

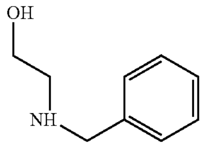 [SMILES: OCCNCc1ccccc1]

with (S)-(+)-epichlorohydrin to form a chlorohydrin compound of formula

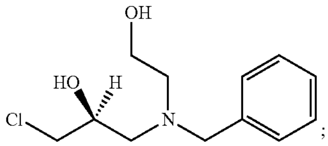 [SMILES: OCCN(Cc1ccccc1)C[C@H](O)CCl]
;

(b) contacting the chlorohydrin compound with a base and a phase transfer catalyst to form an epoxide compound of formula

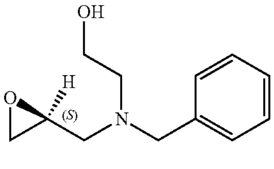
;

(c) contacting the epoxide compound with base and a compound of formula:

(Ia)

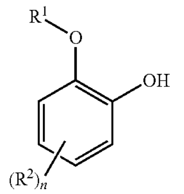

to form a diol compound of formula (IIa)

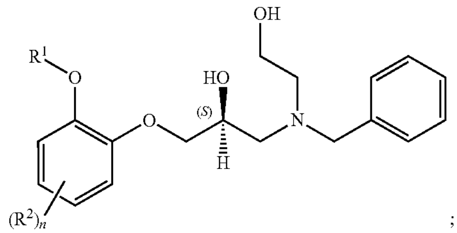

;

(d) contacting the diol compound with a base followed by addition of a sulfonyl halide compound to form an intermediate sulfonate of formula (IIa')

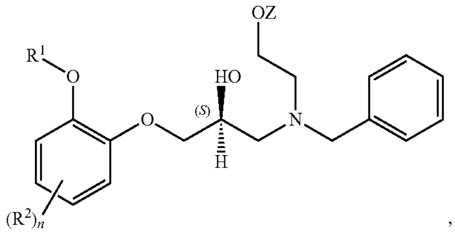

, wherein Z is a sulfonyl leaving group, that cyclizes in situ to form an N-benzyl protected morpholine compound of formula (IIb)

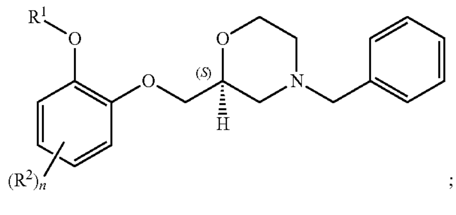

;

(e) forming the HCl salt of the compound of formula (IIb) and recrystallizing it to afford the highly pure (S)-enantiomer as an HCl salt;

(f) converting the HCl salt of compound (IIb) to the free base;

(g) contacting the N-benzyl protected morpholine compound with a chloroformate of formula:

(Ic)

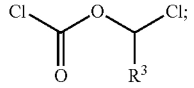

to form an intermediate N-benzyl chlorocarbamate salt of formula (IIc)

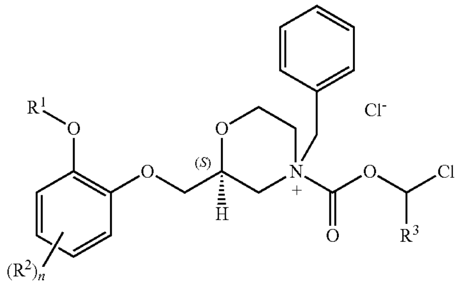

that loses benzyl chloride upon heating to give a compound of formula (IId)

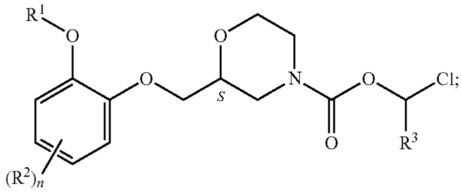

(h) addition of the chlorocarbamate compound to a metal salt of an amino acid derivative of formula (Id)

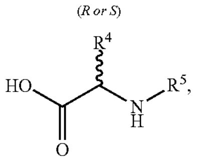

wherein the amino acid derivative has been pretreated with a metal compound carbonate, to form a protected amine of formula (IIe)

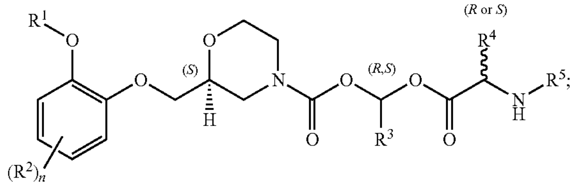

and, (i) contacting the protected amine with an acid to provide the morpholine derivative having the following formula:

(IIf)

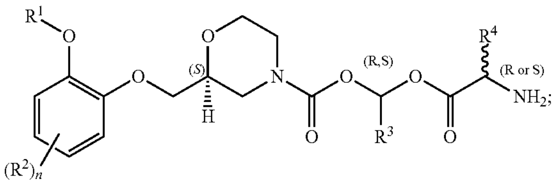

wherein $R^1$ is $C_1$-$C_6$ alkyl, aryl, heteroaryl, or heterocycloalkyl; each $R^2$ is independently selected from F, Cl, Br, I, CN, $NO_2$, $C_1$-$C_6$ alkyl, aryl, heteroaryl, or heterocycloalkyl; $R^3$ is a $C_1$-$C_6$ alkyl, $R^4$ is a $C_1$-$C_6$ alkyl, $R^5$ is an amino protecting group; and n is 0, 1, 2, 3, or 4.

In an embodiment, the invention provides a method of manufacturing a morpholine derivative of formula (IIe):

(IIe)

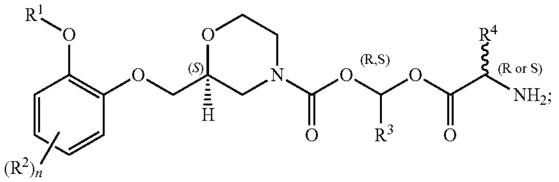

or a prodrug or a pharmaceutically acceptable salt thereof, the method comprising:

(a) reacting a compound of formula

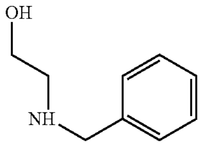 [SMILES: OCCNCc1ccccc1]

with (S)-(+)-epichlorohydrin to form a chlorohydrin compound of formula

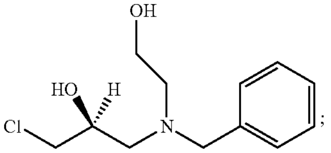

(b) contacting the chlorohydrin compound with a base and a phase transfer catalyst to form an epoxide compound of formula

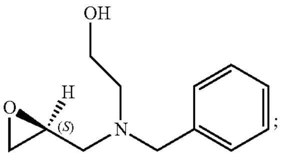

(c) contacting the epoxide compound with base and a compound of formula:

(Ia)

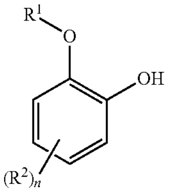

to form a diol compound of formula (IIa)

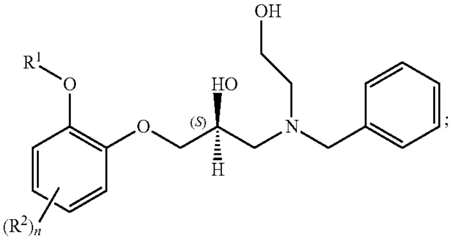

(d) contacting the diol compound with a base followed by addition of a sulfonyl halide to form an intermediate sulfonate of formula (IIa')

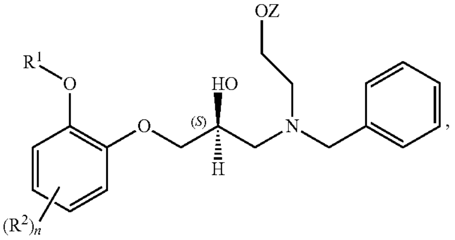

wherein Z is a sulfonyl leaving group; that cyclizes in situ to form an N-benzyl protected morpholine compound of formula (IIb)

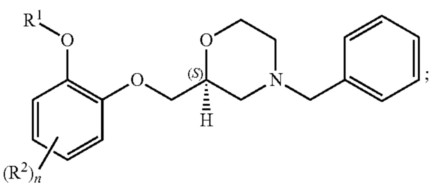

(e) forming the HCl salt of the compound of formula (IIb) and recrystallizing it to afford the highly pure (S)-enantiomer as an HCl salt;

(f) converting the HCl salt of compound (IIb) to the free base;

(g) contacting the N-benzyl protected morpholine compound with a chloroformate of formula:

(Ic)

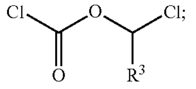

to form an intermediate N-benzyl chlorocarbamate salt of formula (IIc)

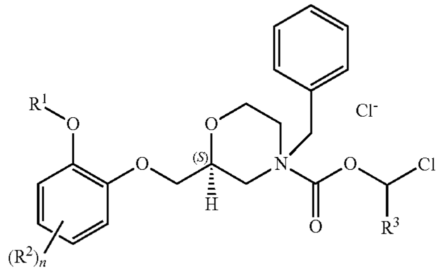

that loses benzyl chloride upon heating to give a compound of formula (IId)

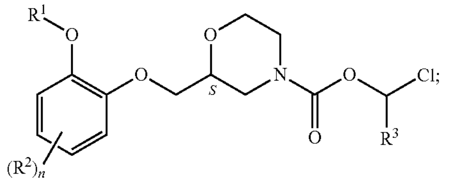

(h) addition of the chlorocarbamate compound to the metal salt of an amino acid derivative of formula (Id)

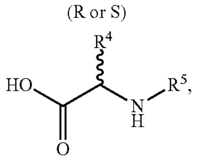

wherein the amino acid derivative has been pretreated with a metal compound, to form a protected amine of formula (IIe)

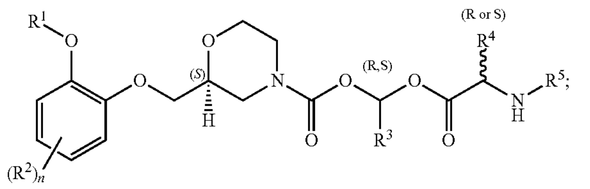

and (i) contacting the protected amine with an acid to provide the morpholine derivative having the following formula:

(IIf)

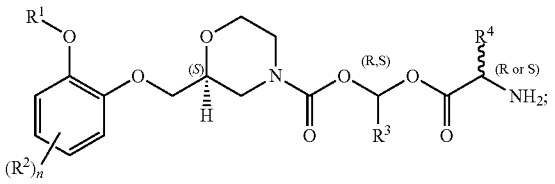

wherein $R^1$ is $C_1$-$C_6$ alkyl, aryl, or heteroaryl; each $R^2$ is independently selected from F, Cl, Br, I, CN, $C_1$-$C_6$ alkyl, aryl, or heteroaryl; $R^3$ is a $C_1$-$C_6$ alkyl, $R^4$ is a $C_1$-$C_6$ alkyl, $R^5$ is an amino protecting group; and n is 0, 1, 2, 3, or 4.

Additional features may be understood by referring to the accompanying drawings, which should be read in conjunction with the following detailed description and examples.

DETAILED DESCRIPTION

Definitions

Figure 1:
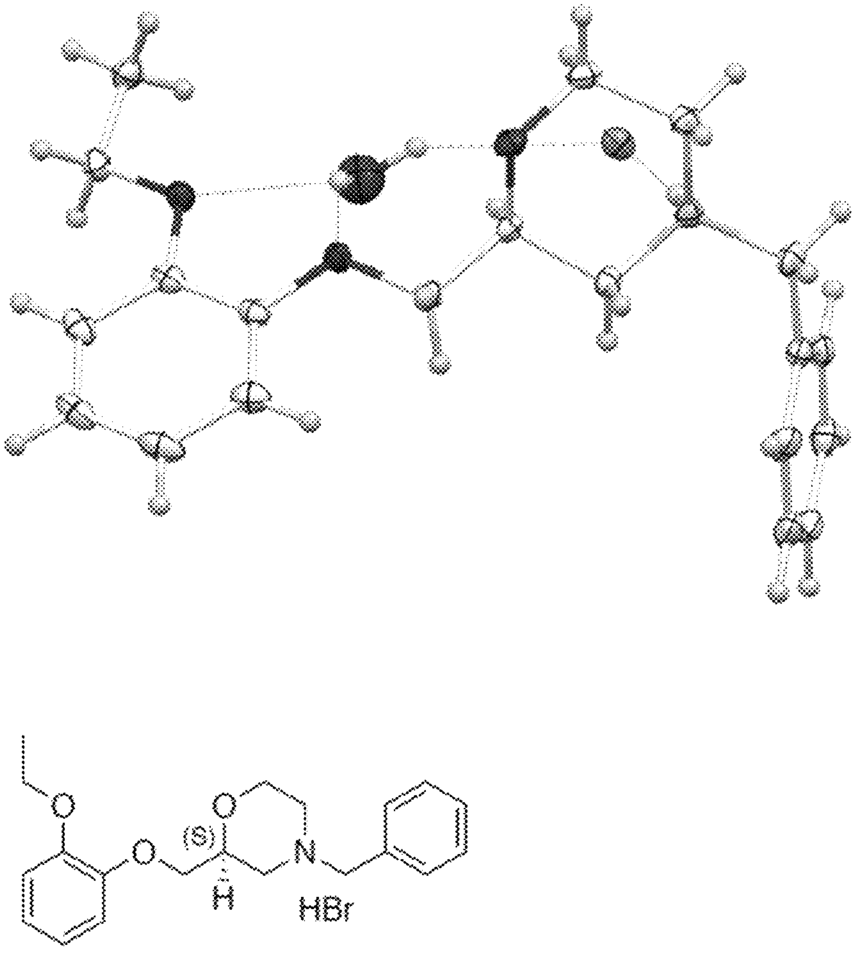
FIG. 1. shows X-Ray structure of (S)-4-benzyl-2-((2-ethoxyphenoxy)methyl)morpholine HBr.

The following terms are used throughout as defined below.

As used herein and in the appended claims, singular articles such as "a" and "an" and "the" and similar referents in the context of describing the elements (especially in the context of the following claims) are to be construed to cover both the singular and the plural, unless otherwise indicated herein or clearly contradicted by context. Recitation of ranges of values herein merely intended to serve as shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

Generally, reference to a certain element such as hydrogen or H is meant to include all isotopes of that element. For example, if an R group is defined to include hydrogen or H, it also includes deuterium and tritium. Compounds comprising radioisotopes such as tritium, $C^{14}$, $P^{32}$, and $S^{35}$ are thus within the scope of the present technology. Procedures for inserting such labels into the compounds of the present technology will be readily apparent to those skilled in the art based on the disclosure herein.

In general, "substituted" refers to an organic group as defined below (e.g., an alkyl group) in which one or more bonds to a hydrogen atom contained therein are replaced by a bond to non-hydrogen or non-carbon atoms. Substituted groups also include groups in which one or more bonds to a carbon(s) or hydrogen(s) atom are replaced by one or more bonds, including double or triple bonds, to a heteroatom. Thus, a substituted group is substituted with one or more substituents, unless otherwise specified. In some embodiments, a substituted group is substituted with 1, 2, 3, 4, 5, or 6 substituents. Examples of substituent groups include: halogens (i.e., F, Cl, Br, and I); hydroxyls; alkoxy, alkenoxy, aryloxy, aralkyloxy, heterocycloalkyl, heterocycloalkyl-alkyl, heterocycloalkyl-oxy, and heterocycloalkyl-alkoxy groups; carbonyls (oxo); carboxylates; esters; urethanes; oximes; hydroxylamines; alkoxyamines; aralkoxyamines; thiols; sulfides; sulfoxides; sulfones; sulfonyls; pentafluorosulfanyl (i.e., $SF_5$), sulfonamides; amines; N-oxides; hydrazines; hydrazides; hydrazones; azides; amides; ureas; amidines; guanidines; enamines; imides; isocyanates; isothiocyanates; cyanates; thiocyanates; imines; nitro groups; nitriles (i.e., CN); and the like.

As used herein, "alkyl" groups include straight chain and branched alkyl groups having from 1 to about 20 carbon atoms, and typically from 1 to 12 carbons or, in some embodiments, from 1 to 8 carbon atoms. As employed herein, "alkyl groups" include cycloalkyl groups as defined below. Alkyl groups may be substituted or unsubstituted. Examples of straight chain alkyl groups include methyl, ethyl, n-propyl, n-butyl, n-pentyl, n-hexyl, n-heptyl, and n-octyl groups. Examples of branched alkyl groups include, but are not limited to, isopropyl, sec-butyl, t-butyl, neopentyl, and isopentyl groups. Representative substituted alkyl groups may be substituted one or more times with, for example, amino, thio, hydroxy, cyano, alkoxy, and/or halo groups such as F, Cl, Br, and I groups. As used herein the term haloalkyl is an alkyl group having one or more halo groups. In some embodiments, haloalkyl refers to a perhaloalkyl group.

Cycloalkyl groups are cyclic alkyl groups such as, but not limited to, cyclopropyl, cyclobutyl, cyclopentyl, cyclohexyl, cycloheptyl, and cyclooctyl groups. In some embodiments, the cycloalkyl group has 3 to 8 ring members, whereas in other embodiments the number of ring carbon atoms range from 3 to 5, 6, or 7. Cycloalkyl groups may be substituted or unsubstituted. Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like. Cycloalkyl groups also include rings that are substituted with straight or branched chain alkyl groups as defined above. Representative substituted cycloalkyl groups may be mono-substituted or substituted more than once, such as, but not limited to: 2,2-; 2,3-; 2,4-; 2,5-; or 2,6-disubstituted cyclohexyl groups or mono-, di-, or tri-substituted norbornyl or cycloheptyl groups, which may be substituted with, for example, alkyl, alkoxy, amino, thio, hydroxy, cyano, and/or halo groups.

Alkenyl groups are straight chain, branched or cyclic alkyl groups having 2 to about 20 carbon atoms, and further including at least one double bond. In some embodiments alkenyl groups have from 1 to 12 carbons, or, typically, from 1 to 8 carbon atoms. Alkenyl groups may be substituted or unsubstituted. Alkenyl groups include, for instance, vinyl, propenyl, 2-butenyl, 3-butenyl, isobutenyl, cyclohexenyl, cyclopentenyl, cyclohexadienyl, butadienyl, pentadienyl, and hexadienyl groups among others. Alkenyl groups may be substituted similarly to alkyl groups. Divalent alkenyl groups, i.e., alkenyl groups with two points of attachment, include, but are not limited to, $CH—CH{=}CH_2$, $C{=}CH_2$, or $C{=}CHCH_3$.

As used herein, "aryl", or "aromatic," groups are cyclic aromatic hydrocarbons that do not contain heteroatoms. Aryl groups include monocyclic, bicyclic and polycyclic ring systems. Thus, aryl groups include, but are not limited to, phenyl, azulenyl, heptalenyl, biphenylenyl, indacenyl, fluorenyl, phenanthrenyl, triphenylenyl, pyrenyl, naphthacenyl, chrysenyl, biphenyl, anthracenyl, indenyl, indanyl, pentalenyl, and naphthyl groups. In some embodiments, aryl groups contain 6-14 carbons, and in others from 6 to 12 or even 6-10 carbon atoms in the ring portions of the groups. The phrase "aryl groups" includes groups containing fused rings, such as fused aromatic-aliphatic ring systems (e.g., indanyl, tetrahydronaphthyl, and the like). Aryl groups may be substituted or unsubstituted.

As used herein, "heteroaryl" refers to a cyclic aromatic compound that contains one or more heteroatoms selected from the group consisting of nitrogen, oxygen, and sulfur in the ring. The "heteroaryl" group can be made up of two or more fused rings (rings that share two adjacent atoms). When the heteroaryl is a fused ring system, then the ring that is connected to the rest of the molecule has a fully delocalized pi-electron system. The other ring(s) in the fused ring system may or may not have a fully delocalized pi-electron system. Examples of heteroaryl rings include, without limitation, furan, thiophene, phthalazinone, pyrrole, oxazole, thiazole, imidazole, pyrazole, isoxazole, isothiazole, triazole, thiadiazole, pyridine, pyridazine, pyrimidine, pyrazine and triazine.

Wherever "hetero" is used it is intended to mean a group as specified, such as an alkyl or an aryl group, where at least one carbon atom has been replaced with a heteroatom selected from nitrogen, oxygen and sulfur.

As used herein, "heterocycloalkyl," refers to a ring having in the ring system one or more heteroatoms independently selected from nitrogen, oxygen and sulfur. The ring may also contain one or more double bonds provided that they do not form a fully delocalized pi-electron system in the rings. The ring defined herein can be a stable 3- to 18-membered ring that consists of carbon atoms and from one to five heteroatoms selected from the group consisting of nitrogen, oxygen, and sulfur. Heterocycloalkyl groups of the presently disclosed compounds may be unsubstituted or substituted. When substituted, the substituent(s) may be one or more groups independently selected from the group consisting of halogen, hydroxy, protected hydroxy, cyano, nitro, alkyl, alkoxy, acyl, acyloxy, carboxy, protected carboxy, amino, protected amino, carboxamide, protected carboxamide, alkylsulfonamido and trifluoromethane-sulfonamido. The "heterocycloalkyl" group can be made up of two or more fused rings (rings that share two adjacent carbon atoms). When the heterocycloalkyl is a fused ring system, then the ring that is connected to the rest of the molecule is a heterocycloalkyl as defined above. The other ring(s) in the fused ring system may be a cycloalkyl, a cycloalkenyl, an aryl, a heteroaryl, or a heterocycloalkyl.

The term "carboxylate" as used herein refers to the conjugate base a carboxylic acid with the chemical formula —COO.

The term "ester" as used herein refers to $—COOR^b—$ and —C(O)O-G groups. $R^b$ is a substituted or unsubstituted alkyl, cycloalkyl, alkenyl, alkynyl, aryl, aralkyl, heterocycloalkyl-alkyl or heterocycloalkyl group as defined herein. G is a carboxylate protecting group. Carboxylate protecting groups are well known to one of ordinary skill in the art. An extensive list of protecting groups for the carboxylate group functionality may be found in Protective Groups in Organic Synthesis, Greene, T. W.; Wuts, P. G. M., John Wiley & Sons, New York, NY, (3rd Edition, 1999) which can be added or removed using the procedures set forth therein and which is hereby incorporated by reference in its entirety and for any and all purposes as if fully set forth herein.

The term "amide" (or "amido") includes C- and N-amide groups, i.e., $C(O)NR^cR^d$, and —NRC(O)—R groups, respectively. $R^c$ and $R^d$ are independently hydrogen, or a substituted or unsubstituted alkyl, alkenyl, alkynyl, cycloalkyl, aryl, aralkyl, heterocycloalkyl-alkyl or heterocycloalkyl group as defined herein. Amido groups therefore include but are not limited to carbamoyl groups ($—C(O)NH_2$) and formamide groups (NHC(O)H). In some embodiments, the amide is —NRC(O)—($C_{1-5}$ alkyl) and the group is termed "carbonylamino," and in others the amide is —NHC(O)-alkyl and the group is termed "alkanoylamino."

The term "amine" (or "amino") as used herein refers to $—NR^eR^f$ groups, wherein $R^c$ and $R^f$ are independently hydrogen, or a substituted or unsubstituted alkyl, alkenyl, alkynyl, cycloalkyl, aryl, aralkyl, heterocycloalkyl-alkyl or heterocycloalkyl group as defined herein. In some embodiments, the amine is alkylamino, dialkylamino, arylamino, or alkylarylamino. In other embodiments, the amine is $NH_2$, methylamino, dimethylamino, ethylamino, diethylamino, propylamino, isopropylamino, phenylamino, or benzylamino.

The term "halogen" or "halo" as used herein refers to bromine (Br), chlorine (Cl), fluorine (F), or iodine (I). In some embodiments, the halogen is chlorine (Cl).

The term "polypeptide" or "peptide" as used herein refers to two or more amino acids linked by a peptide (i.e., amide) bond between the carboxyl terminus of one amino acid and the amino terminus of another. The term "peptide" may be combined with a prefix indicating the number of amino acids in the peptide, e.g., a "pentapeptide" is a peptide of five amino acids.

The term "amino acid" is recognized in the art and generally refers to a natural or unnatural alpha or beta amino acid. The term "amino acid" includes, but is not limited to, any one of the standard L-amino acids commonly found in naturally occurring peptides or to unnatural amino acids, the D-isomers of amino acids or racemic amino acids.

The term "amino acid residue with hydrophobic side chain" as used herein refers to the following amino acids: alanine (Ala), valine (Val), isoleucine (Ile), leucine (Leu), methionine (Met), phenylalanine (Phe), tyrosine (Tyr), tryptophan (Trp); or to unnatural amino acids including but not limited to, norleucine, norvaline, cyclohexylalanine, cyclohexylglycine, cyclopentylglycine and the like. In some embodiments, the amino acid residue with hydrophobic side chain is valine (Val). In other embodiments, the amino acid residue may be racemic or chiral (an L-amino acid (S-configuration) or a D-amino acid (R-configuration)), such as L-valine ((S)-valine) or D-valine ((R)-valine)).

The term "acetyl" as used herein refers to a methyl group bonded to a carbonyl group ($CH_3CO—$).

Pharmaceutically acceptable salts of compounds described herein are within the scope of the present technology and include acid or base addition salts which retain the desired pharmacological activity and is not biologically undesirable (e.g., the salt is not unduly toxic, allergenic, or irritating, and is bioavailable). When the compound of the present technology has a basic group, such as, for example, an amino group, pharmaceutically acceptable salts can be formed with inorganic acids (such as hydrochloric acid, hydroboric acid, nitric acid, sulfuric acid, and phosphoric acid), organic acids (e.g., alginate, formic acid, acetic acid, benzoic acid, gluconic acid, fumaric acid, oxalic acid, tartaric acid, lactic acid, maleic acid, citric acid, succinic acid, malic acid, methanesulfonic acid, benzenesulfonic acid, naphthalene sulfonic acid, and p-toluenesulfonic acid) or acidic amino acids (such as aspartic acid and glutamic acid). When the compound of the present technology has an acidic group, such as for example, a carboxylic acid group, it can form salts with metals, such as alkali and earth alkali metals (e.g., $Na^+$, $K^+$, $Ca^{2+}$, $Mg^{2+}$, or $Zn^{2+}$), ammonia or organic amines (e.g., dicyclohexylamine, trimethylamine, triethylamine, pyridine, picoline, ethanolamine, diethanolamine, or triethanolamine) or basic amino acids (e.g. arginine, lysine, or ornithine). Such salts can be prepared in situ during isolation and purification of the compounds or by separately reacting the purified compound in its free base or free acid form with a suitable acid or base, respectively, and isolating the salt thus formed.

Stereoisomers of compounds (also known as optical isomers) include all chiral, diastereomeric, and racemic forms of a structure, unless the specific stereochemistry is expressly indicated. Thus, compounds used in the present technology include enriched or resolved optical isomers at any or all asymmetric atoms as are apparent from the depictions. Both racemic and diastereomeric mixtures, as well as the individual optical isomers can be isolated or synthesized so as to be substantially free of their enantiomeric or diastereomeric partners, and these stereoisomers are all within the scope of the present technology.

The term "pharmaceutically acceptable excipient" refers to those substances that are well accepted by the industry and regulatory agencies such as those listed in monographs published in compendia such as USP-NF, Food Chemicals Codex, Code of Federal Regulations (CFR), FDA Inactive Ingredients Guide and in 21 CFR parts 182 and 184 that lists substances that are generally regarded as safe (GRAS) food ingredients.

Methods

Provided herein are novel methods of manufacture of morpholine derivatives, prodrugs, and pharmaceutically acceptable salts thereof with improved synthetic methods, control of stereochemistry, and reduction of impurities to thereby provide materials suitable for pharmaceutical applications.

In one aspect provided herein is a method of manufacturing a morpholine derivative of formula (IIb):

(IIb)

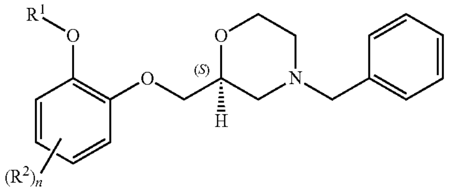

;

or a pharmaceutically acceptable salt thereof, the method including:

(a) reacting a compound of formula

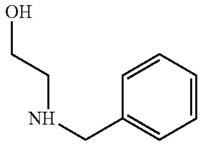 [SMILES: OCCNCc1ccccc1]

with (S)-(+)-epichlorohydrin to form a chlorohydrin compound of formula

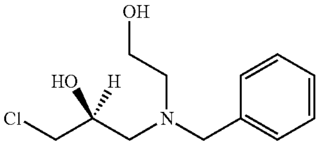

;

(b) contacting the chlorohydrin compound with a base and a phase transfer catalyst to form an epoxide compound of formula

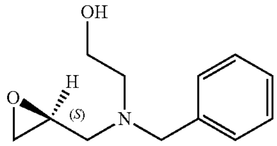

;

(c) contacting the epoxide compound with a base and a compound of formula:

(Ia)

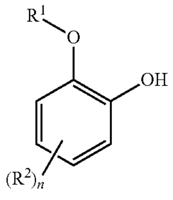

to form a diol compound of formula (IIa)

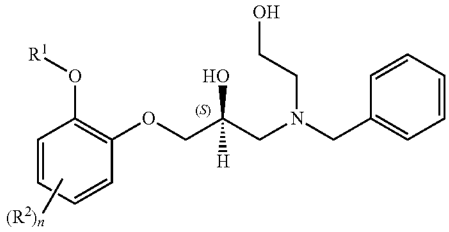

;

and (d) contacting the diol compound with a base followed by addition of a sulfonyl halide compound to form an intermediate sulfonate of formula (IIa')

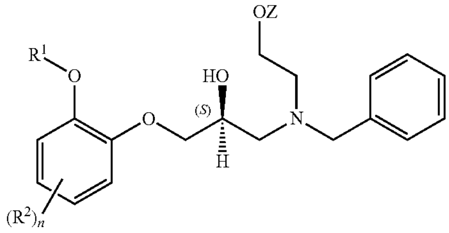

;

wherein Z is a sulfonyl leaving group, that cyclizes in situ to give an N-benzyl protected morpholine compound of formula (IIb):

(IIb)

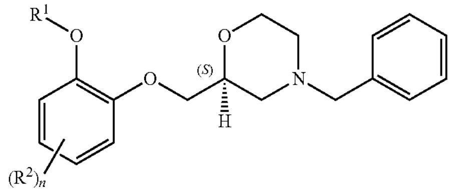

;

and (e) forming the HCl salt of the compound of formula IIb and recrystallizing it to afford the highly pure (S)-enantiomer HCl salt;

wherein $R^1$ is $C_1$-$C_6$ alkyl, aryl, heteroaryl, or heterocycloalkyl; and each $R^2$ is independently selected from F, Cl, Br, I, CN, $NO_2$, $C_1$-$C_6$ alkyl, aryl, heteroaryl, or heterocycloalkyl; and n is 0, 1, 2, 3, or 4.

In another aspect provided herein is a method of manufacturing a morpholine derivative or prodrug or a pharmaceutically acceptable salt thereof, the method comprising:

(a) reacting a compound of formula

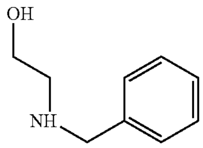 [SMILES: OCCNCc1ccccc1]

with (S)-(+)-epichlorohydrin to form a chlorohydrin compound of formula

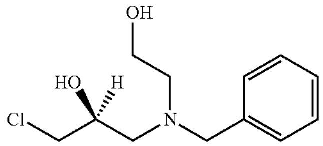
;

(b) contacting the chlorohydrin compound with a base and phase transfer catalyst to form an epoxide compound of formula

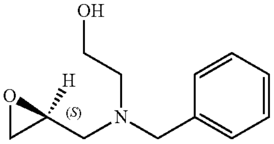
;

(c) contacting the epoxide compound with base and a compound of formula:

(Ia)

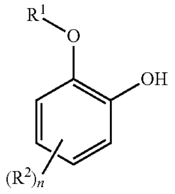

to form a diol compound of formula (IIa)

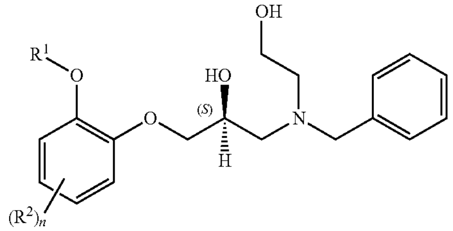
;

(d) contacting the diol compound with a base and a sulfonyl halide to form an intermediate sulfonate that cyclizes to form an N-benzyl protected morpholine compound of formula (IIb)

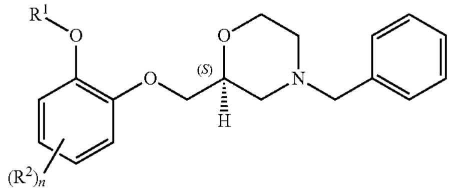
;

(e) forming the HCl salt of the compound of formula (IIb) and recrystallizing it to afford the highly pure (S)-enantiomer as an HCl salt; and (f) converting the HCl salt of compound (IIb) to the free base;

(g) contacting the N-benzyl protected morpholine compound with a chloroformate of formula:

(Ic)

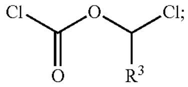

to form an intermediate N-benzyl chlorocarbamate salt of the formula (IIc)

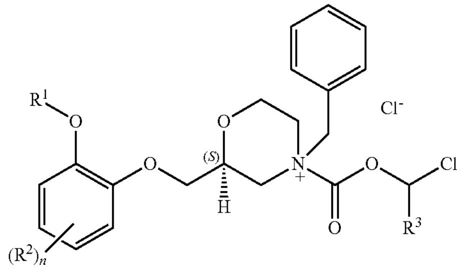

that loses benzyl chloride upon heating to give a compound of formula (IId)

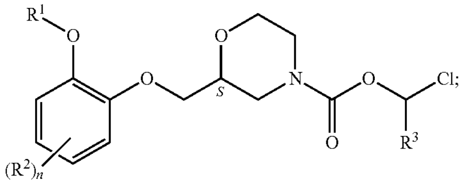

(h) addition of the chlorocarbamate compound to the metal salt of an amino acid derivative of formula (Id)

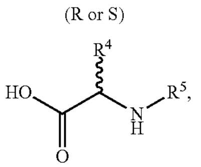

wherein the amino acid derivative has been pretreated with a metal compound, to form a protected amine of formula (IIe)

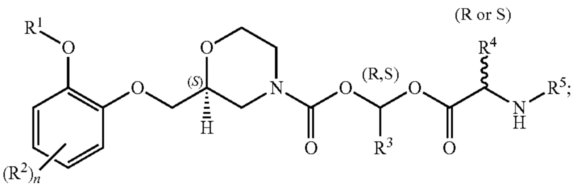

and (i) contacting the protected amine with an acid to provide the morpholine derivative having the following formula:

(IIf)

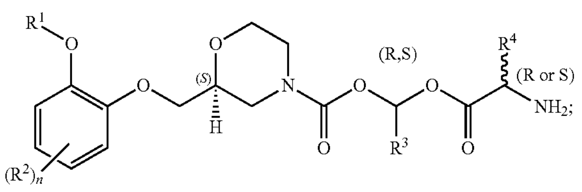

wherein $R^1$ is $C_1$-$C_6$ alkyl, aryl, heteroaryl, or heterocycloalkyl; each $R^2$ is independently selected from F, Cl, Br, I, CN, $NO_2$, $C_1$-$C_6$ alkyl, aryl, heteroaryl, or heterocycloalkyl; $R^3$ is a $C_1$-$C_6$ alkyl, $R^4$ is a $C_1$-$C_6$ alkyl, $R^5$ is an amino protecting group; and n is 0, 1, 2, 3, or 4.

For the sake of convenience and without putting any limitations thereof, the methods of manufacture of the morpholine derivatives have been separated into several steps, each step being disclosed herein in a multiplicity of non-limiting embodiments. These steps comprise Steps a), b), c), d), e), f), g), h), and i) as depicted above.

The above-mentioned steps will be considered below in more detail.

The process of Step a) may be advantageously carried out in the presence of a solvent. In some embodiments, the solvent is methanol. Alternatively, the process may be heated. In embodiments, the reaction is heated to a temperature of about 35° C.

The process of Step b) may be advantageously carried out in the presence of a phase-transfer catalyst. The process may be advantageously carried out in the presence of a base. In some embodiments the base is NaOH. The process may include one or more solvents as part of a solvent system. In some embodiments, the solvent system is a liquid-liquid biphasic system. In some embodiments, the solvent system is a monophasic liquid system. In some embodiments, the liquid-liquid biphasic system comprises water. In some embodiments, the liquid-liquid biphasic system comprises methyl tertiary-butyl ether (MTBE). The phase transfer catalyst can be selected from quaternary ammonium salts, such as benzyltrimethylammonium salts, tetrabutylammonium salts or other phase transfer catalysts known in the art. In a preferred embodiment, the phase transfer catalyst is tetrabutylammonium hydrogen sulfate. In some embodiments, the process may be run at room temperature.

The process of Step c) may be advantageously carried out in the presence of a base. In some embodiments the base is $Cs_2CO_3$. In some embodiments, the base may be added portionwise. The process may include one or more solvents as part of a solvent system. In some embodiments, the solvent system is a monophasic liquid system. In some embodiments, solvent is toluene. Alternatively, the process may be heated upon completion of addition of base. In some embodiments, the process may heated to a temperature of about 110° C.

The process of Step d) may be advantageously carried out in the presence of a phase-transfer catalyst. The process may be carried out in the presence of a base. The base may be a solid or a liquid. In some embodiments the base is NaOH. The process may include one or more solvents as part of a solvent system. In some embodiments, the solvent system is a monophasic liquid system. In some embodiments, solvent is toluene. Alternatively, the process may be heated upon completion of addition of base. In some embodiments, the process may heated to a temperature of about 30° C. In some embodiments, the sulfonyl halide compound is selected from the group consisting of p-toluenesulfonyl chloride (tosyl chloride), brosyl chloride, nosyl chloride, and mesyl chloride. In some embodiments, the sulfonyl halide compound is p-toluenesulfonyl chloride (tosyl chloride). Further, after the period of heating, the process may be cooled to a reduced temperature prior to the addition of p-toluenesulfonyl chloride. In some embodiments, the process is cooled to a temperature of about 20° C. In some embodiments, the p-toluenesulfonyl chloride is added portionwise. The phase transfer catalyst can be selected from quaternary ammonium salts, such as benzyltrimethylammonium salts, tetrabutylammonium salts or other phase transfer catalysts known in the art. In a preferred embodiment, the phase transfer catalyst is benzyl triethylammonium chloride. The solid or liquid base can be a carbonate such as alkali carbonate, NaOH, KOH, tetrabutyl ammonium hydroxide, LiOH, amines such as tri-substituted amines (e.g., as triethylamine or tributylamine), DMAP, or other appropriate base. In a preferred embodiment, the base is NaOH. The solvents used in the process include but are not limited to ethers such as methyl t-butyl ether, aromatic solvents (e.g., toluene), or other appropriate solvent. In a preferred embodiment, the solvent is toluene. In one variation, Step d) is carried out in the presence of a phase transfer catalyst in the presence of a solid or liquid base with a solution of the diol in toluene, wherein the reaction is cooled to 20° C. prior to portionwise addition of the p-toluenesulfonyl chloride. After the reaction is complete, the reaction mixture can be washed with water, followed by work-up procedures known in the art. Upon isolation of the N-benzyl protected morpholine product, the product may be treated with HCl to form the HCl salt. In some embodiments, the HCl salt contains greater than 60% of the (S) enantiomer. In some embodiments, the HCl salt contains greater than 75% of the (S) enantiomer. In some embodiments, the HCl salt contains greater than: 90%, 91%, 92%, 93%, 94%, 95%, 96%, 97%, 98%, or 99% of the (S) enantiomer. In some embodiments, the HCl salt contains greater than 95% of the (S) enantiomer. In some embodiments, HCl salt contains greater than 99% of the (S) enantiomer. In some embodiments, the HCl salt has an enantiomeric excess of greater than: 75%. In some embodiments, the HCl salt has enantiomeric excess of greater than: 90%, 91%, 92%, 93%, 94%, 95%, 96%, 97%, 98%, or 99%. In some embodiments, the HCl salt has enantiomeric excess of greater than 95%. In some embodiments, HCl salt has enantiomeric excess of greater than 99%. Variations of this embodiment of the invention are further disclosed in the Examples section (e.g. Example 8).

The process of Step g) may be advantageously carried out in the presence of a solvent. In some embodiments, the solvent is dichloromethane. Alternatively, the process may be cooled prior to the addition of the chloroformate. In embodiments, the reaction is cooled to a temperature of about 0° C.

The process of Step h) may be advantageously carried out in the presence of a solvent. In some embodiments, the solvent is dimethylformamide (DMF). In some embodiments, the metal salt is a cesium salt, a potassium salt, a silver salt, or a mercury salt. In some embodiments, the metal salt is a cesium salt. In some embodiments, the metal compound is a cesium compound, a potassium compound, a silver compound, or a mercury compound. In some embodiments, the metal compound is a cesium compound. In some embodiments, the metal compound is $Cs_2CO_3$, $K_2CO_3$, or $Ag_2CO_3$. In some embodiments, the metal compound is $Cs_2CO_3$. The process may be carried out in the presence of a base. In some embodiments the base is $Cs_2CO_3$. Alternatively, the process may be heated. In embodiments, the reaction is heated to a temperature of about 85° C.

The process of Step i) may be advantageously carried out in the presence of a solvent. In some embodiments, the solvent is ethyl acetate.

In some embodiments, the compound of formula (Ia) is

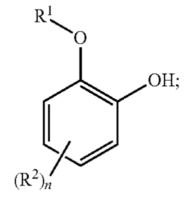

wherein $R^1$ is $C_1$-$C_6$ alkyl, aryl, heteroaryl, or heterocycloalkyl; each $R^2$ is independently selected from F, Cl, Br, I, CN, $NO_2$, $C_1$-$C_6$ alkyl, aryl, heteroaryl, or heterocycloalkyl; and n is 0, 1, 2, 3, or 4. In some embodiments, $R^2$ is independently selected from F, Cl, Br, I, CN, $NO_2$, $C_1$-$C_6$ alkyl, aryl, or heteroaryl. In some embodiments, $R^2$ is independently selected from F, Cl, Br, I, CN, $C_1$-$C_6$ alkyl, aryl, or heteroaryl. In some embodiments, each $R^2$ is independently selected from F, Cl, Br, I, $C_1$-$C_6$ alkyl, or aryl. In some embodiments, each $R^2$ is independently selected from F, Cl, Br, I, or $C_1$-$C_6$ alkyl. In some embodiments, n is 0. In some embodiments, n is 1. In some embodiments, n is 2. In some embodiments, the compound of formula (Ia) is

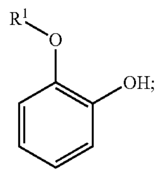

wherein $R^1$ is $C_1$-$C_6$ alkyl, aryl, heteroaryl, or heterocycloalkyl. In some embodiments, $R^1$ is $C_1$-$C_6$ alkyl. In some embodiments, $R^1$ is $CH_2CH_3$. In some embodiments, $R^1$ is $CH_3$. In some embodiments, the compound of formula (Ia) is

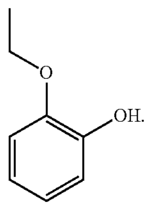

In some embodiments, the compound of formula (IIa) is (IIa)

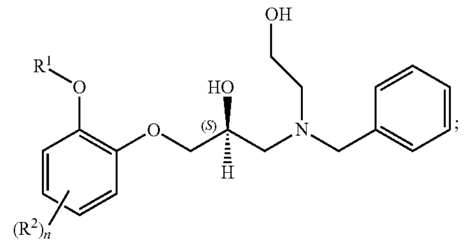

wherein $R^1$ is $C_1$-$C_6$ alkyl, aryl, heteroaryl, or heterocycloalkyl; each $R^2$ is independently selected from F, Cl, Br, I, CN, $NO_2$, $C_1$-$C_6$ alkyl, aryl, heteroaryl, or heterocycloalkyl; and n is 0, 1, 2, 3, or 4. In some embodiments, $R^2$ is independently selected from F, Cl, Br, I, CN, $NO_2$, $C_1$-$C_6$ alkyl, aryl, or heteroaryl. In some embodiments, $R^2$ is independently selected from F, Cl, Br, I, CN, $C_1$-$C_6$ alkyl, aryl, or heteroaryl. In some embodiments, each $R^2$ is independently selected from F, Cl, Br, I, $C_1$-$C_6$ alkyl, or aryl. In some embodiments, each $R^2$ is independently selected from F, Cl, Br, I, or $C_1$-$C_6$ alkyl. In some embodiments, n is 0. In some embodiments, n is 1. In some embodiments, n is 2. In some embodiments, the compound of formula (IIa) is (IIa)

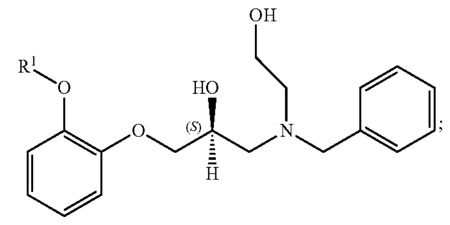

wherein $R^1$ is $C_1$-$C_6$ alkyl, aryl, heteroaryl, or heterocycloalkyl. In some embodiments, $R^1$ is $C_1$-$C_6$ alkyl. In some embodiments, $R^1$ is $CH_2CH_3$. In some embodiments, $R^1$ is $CH_3$. In some embodiments, the compound of formula (IIa) is

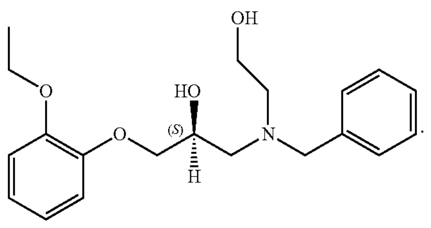

In some embodiments, the compound of formula (IIa') is (IIa')

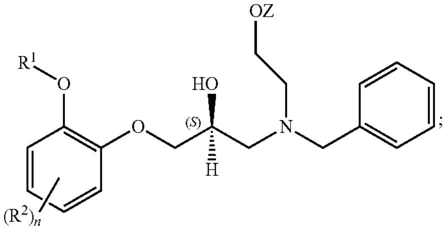

wherein $R^1$ is $C_1$-$C_6$ alkyl, aryl, heteroaryl, or heterocycloalkyl; each $R^2$ is independently selected from F, Cl, Br, I, CN, $NO_2$, $C_1$-$C_6$ alkyl, aryl, heteroaryl, or heterocycloalkyl; Z is a sulfonyl leaving group; and n is 0, 1, 2, 3, or 4. In some embodiments, $R^2$ is independently selected from F, Cl, Br, I, CN, $NO_2$, $C_1$-$C_6$ alkyl, aryl, or heteroaryl. In some embodiments, $R^2$ is independently selected from F, Cl, Br, I, CN, $C_1$-$C_6$ alkyl, aryl, or heteroaryl. In some embodiments, each $R^2$ is independently selected from F, Cl, Br, I, $C_1$-$C_6$ alkyl, or aryl. In some embodiments, each $R^2$ is independently selected from F, Cl, Br, I, or $C_1$-$C_6$ alkyl. In some embodiments, Z is

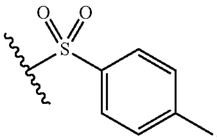,
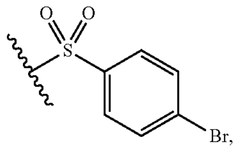,
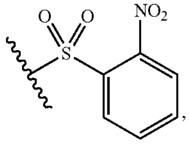,
or
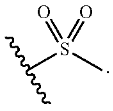.

In some embodiments, Z is

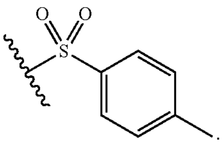 [SMILES: *S(=O)(=O)c1ccc(C)cc1].

In some embodiments, n is 0. In some embodiments, n is 1. In some embodiments, n is 2. In some embodiments, the compound of formula (IIa) is (IIa)

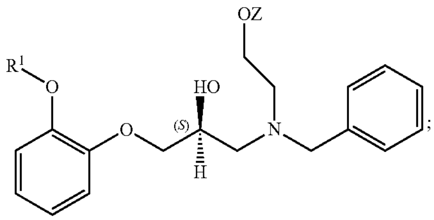

wherein $R^1$ is $C_1$-$C_6$ alkyl, aryl, heteroaryl, or heterocycloalkyl and Z is a sulfonyl leaving group. In some embodiments, $R^1$ is $C_1$-$C_6$ alkyl. In some embodiments, $R^1$ is $CH_2CH_3$. In some embodiments, $R^1$ is $CH_3$. In some embodiments, the compound of formula (IIa) is

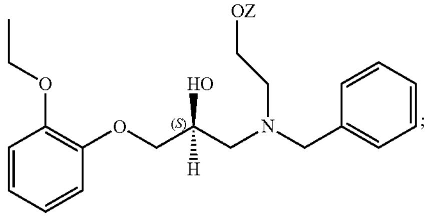

wherein Z is a sulfonyl leaving group.

In some embodiments, the compound of formula (IIb) is (IIb)

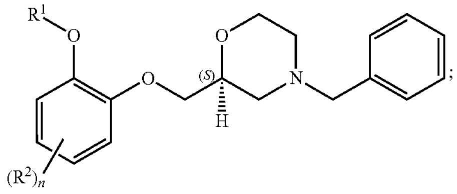

wherein $R^1$ is $C_1$-$C_6$ alkyl, aryl, heteroaryl, or heterocycloalkyl; each $R^2$ is independently selected from F, Cl, Br, I, CN, $NO_2$, $C_1$-$C_6$ alkyl, aryl, heteroaryl, or heterocycloalkyl; and n is 0, 1, 2, 3, or 4. In some embodiments, $R^2$ is independently selected from F, Cl, Br, I, CN, $NO_2$, $C_1$-$C_6$ alkyl, aryl, or heteroaryl. In some embodiments, $R^2$ is independently selected from F, Cl, Br, I, CN, $C_1$-$C_6$ alkyl, aryl, or heteroaryl. In some embodiments, each $R^2$ is independently selected from F, Cl, Br, I, $C_1$-$C_6$ alkyl, or aryl. In some embodiments, each $R^2$ is independently selected from F, Cl, Br, I, or $C_1$-$C_6$ alkyl. In some embodiments, n is 0. In some embodiments, n is 1. In some embodiments, n is 2. In some embodiments, the compound of formula (IIb) is (IIb)

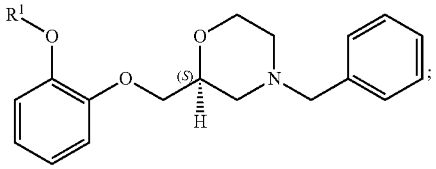

wherein $R^1$ is $C_1$-$C_6$ alkyl, aryl, heteroaryl, or heterocycloalkyl. In some embodiments, $R^1$ is $C_1$-$C_6$ alkyl. In some embodiments, $R^1$ is $CH_2CH_3$. In some embodiments, $R^1$ is $CH_3$. In some embodiments, the compound of formula (IIb) is

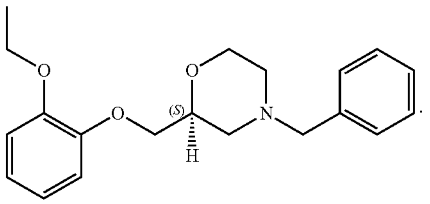

In some embodiments, the compound of formula (Ic) is

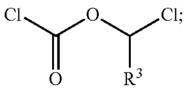

wherein $R^3$ is $C_1$-$C_6$ alkyl. In some embodiments, $R^3$ is —$CH_3$. In some embodiments, $R^3$ is a —$CH_2CH_3$. In some embodiments, $R^3$ is a —$CH(CH_3)_2$. In some embodiments, the compound of formula (Ic) is

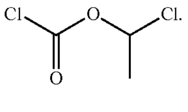

In some embodiments, the compound of formula (Ic) is

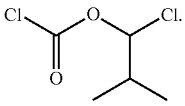

In some embodiments, the compound of formula (IIc) is (IIc)

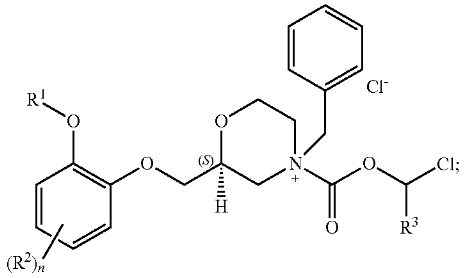

wherein $R^1$ is $C_1$-$C_6$ alkyl, aryl, heteroaryl, or heterocycloalkyl; each $R^2$ is independently selected from F, Cl, Br, I, CN, $NO_2$, $C_1$-$C_6$ alkyl, aryl, heteroaryl, or heterocycloalkyl; $R^3$ is a $C_1$-$C_6$ alkyl, and n is 0, 1, 2, 3, or 4. In some embodiments, $R^2$ is independently selected from F, Cl, Br, I, CN, $NO_2$, $C_1$-$C_6$ alkyl, aryl, or heteroaryl. In some embodiments, $R^2$ is independently selected from F, Cl, Br, I, CN, $C_1$-$C_6$ alkyl, aryl, or heteroaryl. In some embodiments, each $R^2$ is independently selected from F, Cl, Br, I, $C_1$-$C_6$ alkyl, or aryl. In some embodiments, each $R^2$ is independently selected from F, Cl, Br, I, or $C_1$-$C_6$ alkyl. In some embodiments, n is 0. In some embodiments, n is 1. In some embodiments, n is 2. In some embodiments, the compound of formula (IIc) is (IIc)

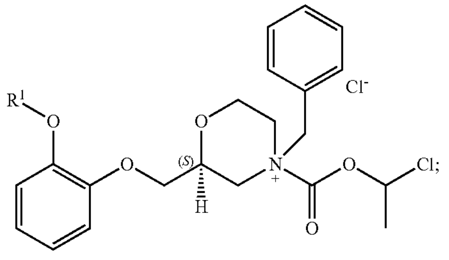

wherein $R^1$ is $C_1$-$C_6$ alkyl, aryl, heteroaryl, or heterocycloalkyl. In some embodiments, $R^1$ is $C_1$-$C_6$ alkyl. In some embodiments, $R^1$ is $CH_2CH_3$. In some embodiments, $R^1$ is $CH_3$. In some embodiments, the compound of formula (IIc) is

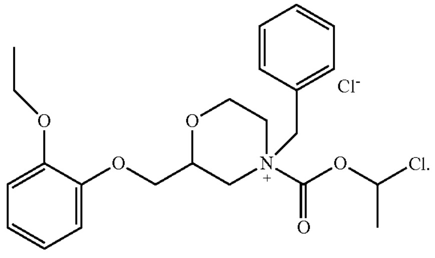

In some embodiments, the compound of formula (IId) is (IId)

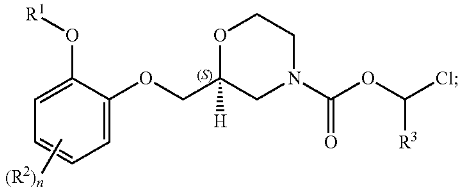

wherein $R^1$ is $C_1$-$C_6$ alkyl, aryl, heteroaryl, or heterocycloalkyl; each $R^2$ is independently selected from F, Cl, Br, I, CN, $NO_2$, $C_1$-$C_6$ alkyl, aryl, heteroaryl, or heterocycloalkyl; $R^3$ is a $C_1$-$C_6$ alkyl, and n is 0, 1, 2, 3, or 4. In some embodiments, $R^2$ is independently selected from F, Cl, Br, I, CN, $NO_2$, $C_1$-$C_6$ alkyl, aryl, or heteroaryl. In some embodiments, $R^2$ is independently selected from F, Cl, Br, I, CN, $C_1$-$C_6$ alkyl, aryl, or heteroaryl. In some embodiments, each $R^2$ is independently selected from F, Cl, Br, I, $C_1$-$C_6$ alkyl, or aryl. In some embodiments, each $R^2$ is independently selected from F, Cl, Br, I, or $C_1$-$C_6$ alkyl. In some embodiments, n is 0. In some embodiments, n is 1. In some embodiments, n is 2. In some embodiments, the compound of formula (IId) is (IId)

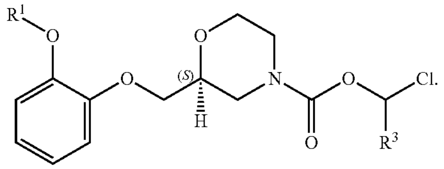

In some embodiments, $R^1$ is $C_1$-$C_6$ alkyl and $R^3$ is a $C_1$-$C_6$ alkyl. In some embodiments, $R^1$ is —$CH_2CH_3$. In some embodiments, $R^1$ is —$CH_3$. In some embodiments, $R^3$ is —$CH_3$. In some embodiments, $R^3$ is —$CH_2CH_3$. In some embodiments, $R^3$ is —$CH(CH_3)_2$. In some embodiments, the compound of formula (IId) is

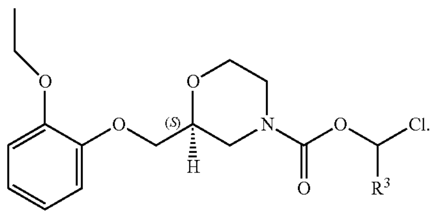

In some embodiments, the compound of formula (IId) is

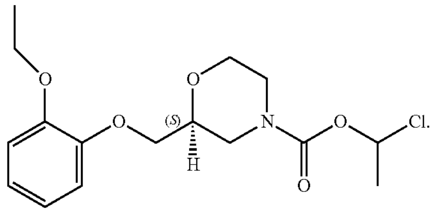

In some embodiments, the compound of formula (IId) is

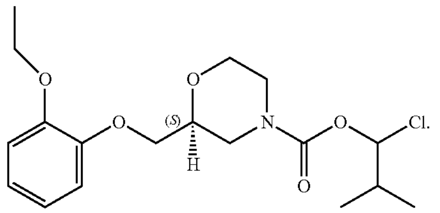

In some embodiments, the compound of formula (Id) is

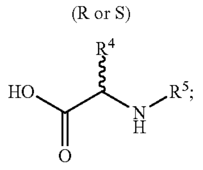

wherein $R^4$ is a $C_1$-$C_6$ alkyl, $R^5$ is an amino protecting group. In some embodiments, the carbon atom with an $R^4$ substituent attached is of the (R) configuration. In some embodiments, the carbon atom with an $R^4$ substituent attached is of the (S) configuration. In some embodiments, the compound of formula (Id) is

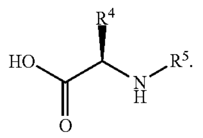

In some embodiments, the compound of formula (Id) is

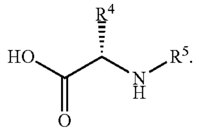

In some embodiments, $R^4$ is —$CH_3$. In some embodiments, $R^4$ is —$CH_2CH_3$. In some embodiments, $R^4$ is —$CH(CH_3)_2$. In some embodiments, the compound of formula (Id) is

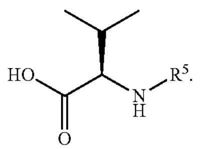

In some embodiments, the compound of formula (Id) is

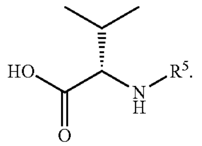

In some embodiments, $R^5$ is t-butoxycarbonyl (Boc). In some embodiments, $R^5$ is carboxybenzyl (Cbz).

In some embodiments, the compound of formula (IIe) is (IIe)

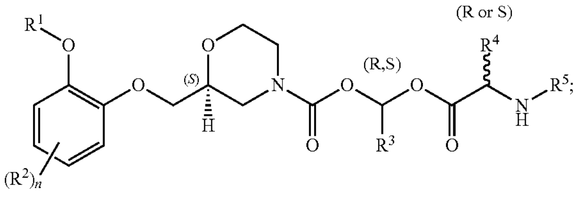

wherein $R^1$ is $C_1$-$C_6$ alkyl, aryl, heteroaryl, or heterocycloalkyl; each $R^2$ is independently selected from F, Cl, Br, I, CN, $NO_2$, $C_1$-$C_6$ alkyl, aryl, heteroaryl, or heterocycloalkyl; $R^3$ is a $C_1$-$C_6$ alkyl, $R^4$ is a $C_1$-$C_6$ alkyl, $R^5$ is an amino protecting group; and n is 0, 1, 2, 3, or 4. In some embodiments, the carbon atom with an $R^4$ substituent attached is of the (R) configuration. In some embodiments, the carbon atom with an $R^4$ substituent attached is of the (S) configuration. In some embodiments, the compound of formula (IIe) is

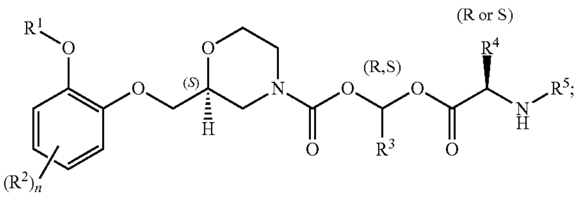

In some embodiments, the compound of formula (IIe) is

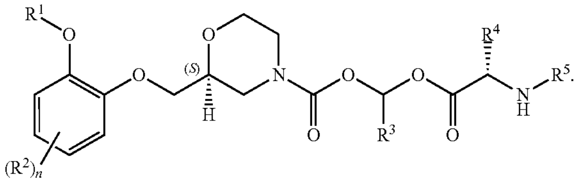

In some embodiments, $R^2$ is independently selected from F, Cl, Br, I, CN, $NO_2$, $C_1$-$C_6$ alkyl, aryl, or heteroaryl. In some embodiments, $R^2$ is independently selected from F, Cl, Br, I, CN, $C_1$-$C_6$ alkyl, aryl, or heteroaryl. In some embodiments, each $R^2$ is independently selected from F, Cl, Br, I, $C_1$-$C_6$ alkyl, or aryl. In some embodiments, each $R^2$ is independently selected from F, Cl, Br, I, or $C_1$-$C_6$ alkyl. In some embodiments, n is 0. In some embodiments, n is 1. In some embodiments, n is 2. In some embodiments, the compound of formula (IIe) is

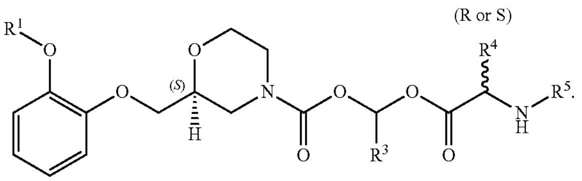

In some embodiments, $R^1$ is $C_1$-$C_6$ alkyl and $R^3$ is a $C_1$-$C_6$ alkyl. In some embodiments, $R^1$ is —$CH_2CH_3$. In some embodiments, $R^1$ is —$CH_3$. In some embodiments, $R^3$ is —$CH_3$. In some embodiments, $R^3$ is —$CH_2CH_3$. In some embodiments, $R^1$ is —$CH(CH_3)_2$. In some embodiments, $R^4$ is —$CH_3$. In some embodiments, $R^4$ is —$CH_2CH_3$. In some embodiments, $R^4$ is —$CH(CH_3)_2$. In some embodiments, $R^5$ is t-butyloxy carbonyl (Boc). In some embodiments, $R^5$ is carboxylbenzyl (Cbz). In some embodiments, the compound of formula (IIe) is

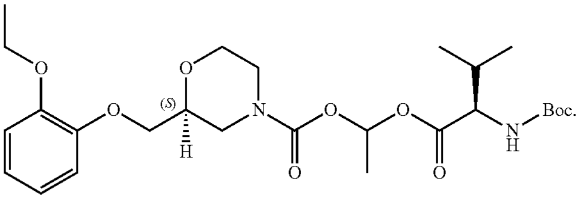

In some embodiments, the compound of formula (IIe) is

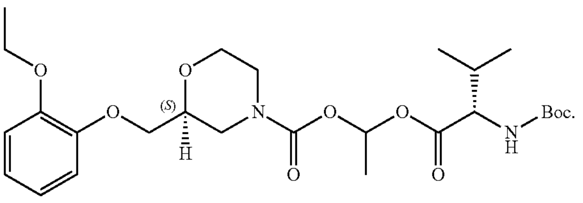

In some embodiments, the compound of formula (IIe) is

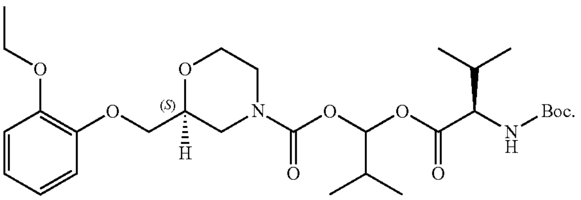

In some embodiments, the compound of formula (IIe) is

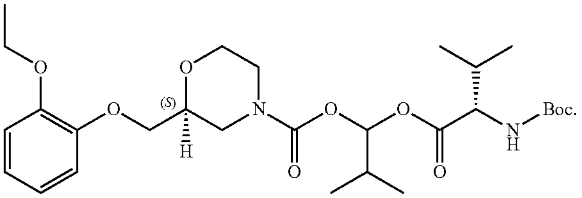

In some embodiments, the compound of formula (IIf) is (IIf)

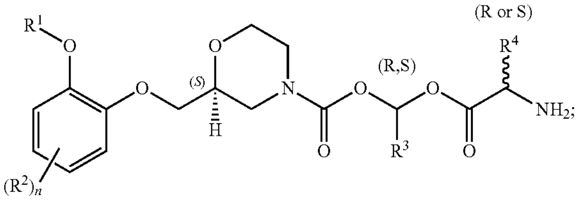

wherein $R^1$ is $C_1$-$C_6$ alkyl, aryl, heteroaryl, or heterocycloalkyl; each $R^2$ is independently selected from F, Cl, Br, I, CN, $NO_2$, $C_1$-$C_6$ alkyl, aryl, heteroaryl, or heterocycloalkyl; $R^3$ is a $C_1$-$C_6$ alkyl, $R^4$ is a $C_1$-$C_6$ alkyl, and n is 0, 1, 2, 3, or 4. In some embodiments, the carbon atom with an $R^4$ substituent attached is of the (R) configuration. In some embodiments, the carbon atom with an $R^4$ substituent attached is of the (5) configuration. In some embodiments, the compound of formula (IIf) is

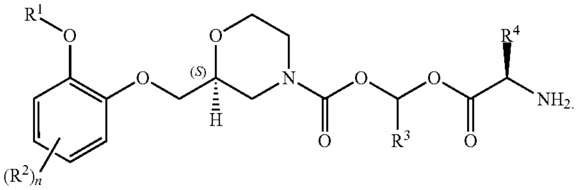

In some embodiments, the compound of formula (IIf) is

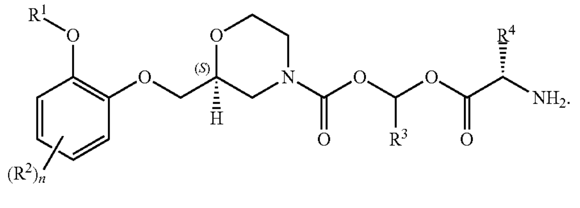

In some embodiments, $R^2$ is independently selected from F, Cl, Br, I, CN, $NO_2$, $C_1$-$C_6$ alkyl, aryl, or heteroaryl. In some embodiments, $R^2$ is independently selected from F, Cl, Br, I, CN, $C_1$-$C_6$ alkyl, aryl, or heteroaryl. In some embodiments, each $R^2$ is independently selected from F, Cl, Br, I, $C_1$-$C_6$ alkyl, or aryl. In some embodiments, each $R^2$ is independently selected from F, Cl, Br, I, or $C_1$-$C_6$ alkyl. In some embodiments, n is 0. In some embodiments, n is 1. In some embodiments, n is 2. In some embodiments, the compound of formula (IIf) is

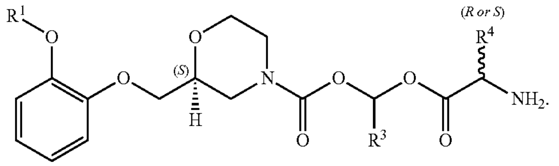

In some embodiments, $R^1$ is $C_1$-$C_6$ alkyl and $R^3$ is a $C_1$-$C_6$ alkyl. In some embodiments, $R^1$ is $—CH_2CH_3$. In some embodiments, $R^1$ is $—CH_3$. In some embodiments, $R^3$ is $—CH_3$. In some embodiments, $R^3$ is $—CH_2CH_3$. In some embodiments, $R^1$ is $—CH(CH_3)_2$. In some embodiments, $R^4$ is $—CH_3$. In some embodiments, $R^4$ is $—CH_2CH_3$. In some embodiments, $R^4$ is $—CH(CH_3)_2$. In some embodiments, the compound of formula (IIf) is

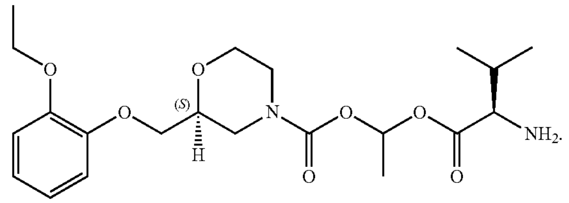

In some embodiments, the compound of formula (IIf) is

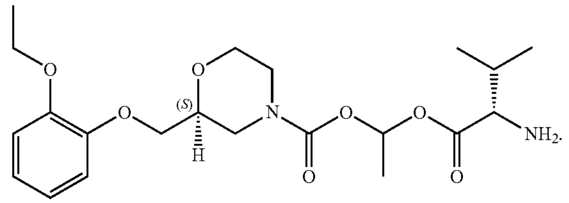

In some embodiments, the compound of formula (IIf) is

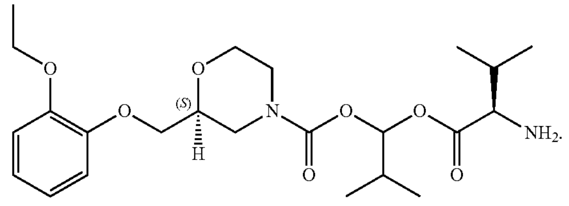

In some embodiments, the compound of formula (IIf) is

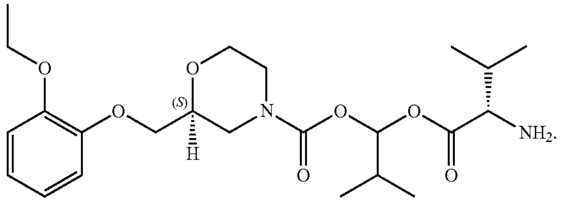

In some embodiments, $R^1$ is $C_1$-$C_6$ alkyl. In some embodiments, $R^1$ is $—CH_3$. In some embodiments, $R^1$ is a $—CH_2CH_3$. In some embodiments, $R^1$ is a $—CH(CH_3)_2$.

In some embodiments, each $R^2$ is independently selected from F, Cl, Br, I, CN, $NO_2$, $C_1$-$C_6$ alkyl, aryl, heteroaryl, or heterocycloalkyl. In some embodiments, $R^2$ is independently selected from F, Cl, Br, I, CN, $NO_2$, $C_1$-$C_6$ alkyl, aryl, or heteroaryl. In some embodiments, $R^2$ is independently selected from F, Cl, Br, I, CN, $C_1$-$C_6$ alkyl, aryl, or heteroaryl. In some embodiments, each $R^2$ is independently selected from F, Cl, Br, I, $C_1$-$C_6$ alkyl, or aryl. In some embodiments, each $R^2$ is independently selected from F, Cl, Br, I, CN, $NO_2$, or $C_1$-$C_6$ alkyl. In some embodiments, each $R^2$ is independently selected from F, Cl, Br, I, or $C_1$-$C_6$ alkyl. In some embodiments, each $R^2$ is independently selected from F, Cl, Br, I, CN, $—CH_3$ or $—CH_2CH_3$. In some embodiments, each $R^2$ is independently selected from F, Cl, Br, I, $—CH_3$. In some embodiments, each $R^2$ is independently aryl, heteroaryl, or heterocycloalkyl. In some embodiments, $R^2$ is F. In some embodiments, $R^2$ is Cl. In some embodiments, $R^2$ is Br. In some embodiments, $R^2$ is I. In some embodiments, $R^2$ is CN. In some embodiments, $R^2$ is $NO_2$. In some embodiments, $R^2$ is $C_1$-$C_6$ alkyl. In some embodiments, $R^2$ is $CH_3$. In some embodiments, $R^2$ is $CH_2CH_3$. In some embodiments, $R^2$ is aryl. In some embodiments, $R^2$ is heteroaryl. In some embodiments, $R^2$ is heterocycloalkyl.

In some embodiments, $R^3$ is $C_1$-$C_6$ alkyl. In some embodiments, $R^3$ is $—CH_3$. In some embodiments, $R^3$ is a $—CH_2CH_3$. In some embodiments, $R^3$ is a $—CH(CH_3)_2$.

In some embodiments, $R^4$ is $C_1$-$C_6$ alkyl. In some embodiments, $R^4$ is $—CH_3$. In some embodiments, $R^4$ is a $—CH_2CH_3$. In some embodiments, $R^4$ is a $—CH(CH_3)_2$.

In some embodiments, $R^5$ is an amino protecting group. In some embodiments, $R^5$ is t-butoxycarbonyl (Boc). In some embodiments, $R^5$ is carboxybenzyl (Cbz). In some embodiments, $R^5$ is 9-fluorenylmethoxycarbonyl (Fmoc). In some embodiments, $R^5$ is benzyl (Bn).

In some embodiments, Z is

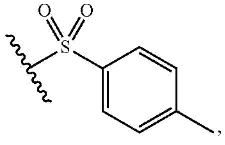,

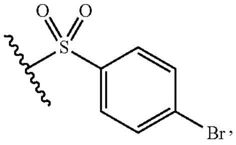,

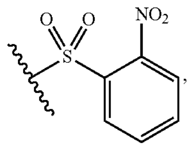, or

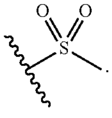.

In some embodiments, Z is

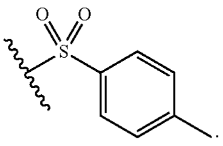 [SMILES: *S(=O)(=O)c1ccc(C)cc1]

In some embodiments, n is 0. In some embodiments, n is 1. In some embodiments, n is 2. In some embodiments, n is 3. In some embodiments, n is 4.

Additional embodiments are illustrated by the following non-limiting examples.

EXAMPLES

Example 1. Synthesis of (S)-2-((2-ethoxyphenoxy)methyl)morpholine

Scheme I.

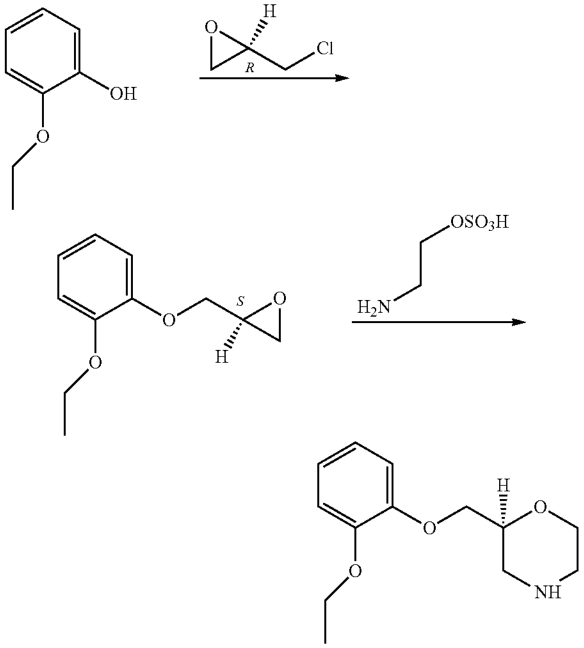

This synthetic route was previously reported in U.S. Granted Patent U.S. Pat. No. 9,403,783B2.

Potassium carbonate (82.93 g, 600 mmol; 3 equiv) and tetrabutylammonium sulfate (3.4 g, 10 mmol 0.05 equiv) were placed in a flask and 74 g (800 mmol; 4 equiv) of R-(−)-epichlorohydrin was added followed by 27.63 g of 2-ethoxyphenol (2, 200 mmol, 1 equiv) dissolved in 30 mL of THF. The mixture was heated to 55° C. overnight under $N_2$. After cooling to room temperature, 300 mL of water was added and the solution extracted with ethyl acetate (3×). The combined extracts were washed with brine (2×), dried over MgSO4 and evaporated. The residual oil was then dissolved in 100 mL of toluene and evaporated (to remove excess epichlorohydrin). This was done a total of 4× to give 50 g of a yellow oil of the epoxyether.

2-Aminoethyl hydrogen sulfate (141 g; 1 mol; 5 equiv) was placed in a 1 L flask and to this was added 7.5 equiv of 60% KOH prepared from 100 g of KOH and 67 mL of water followed by 50 g of the crude epoxyether dissolved in 200 mL of methanol. After 2 hr heating at 55° C., another 7.5 equiv of 60% KOH was added and the mixture heated at 55° C. overnight. After cooling the mixture was evaporated to remove methanol and the residue diluted with water and extracted with ethyl acetate (5×). The combined extract was washed with brine (3×), dried over $MgSO_4$ and evaporated to give crude (S)-2-((2-ethoxyphenoxy)methyl)morpholine free base as a yellow oil (49 g). The crude oil was dissolved in 100 mL of ethanol and 50 mL of 4N HCl in dioxane diluted with 50 mL of ethyl acetate was added, initially giving a clear solution The solid HCl salt precipitated within ca. 2 min and the suspension was kept at room temperature for 5 hr, then the solid salt was filtered off and rinsed with ethyl acetate. The salt was dried in air and on high vacuum to give 17.15 g of (S)-2-((2-ethoxyphenoxy)methyl)morpholine HCl salt. The product was a single peak on HPLC and assayed for 94.58% S by SFC.

The above process was repeated on 200 or 300 mmol scale. After blending the batches and drying the sample on high vacuum, a total of 74.46 g of (S)-2-((2-ethoxyphenoxy)methyl)morpholine HCl was obtained. Chiral SFC analysis showed 92.724% S. Anal. Calcd for $C_{13}H_{20}NO_3Cl$: C, 57.04; H, 7.36; N, 5.12; Cl, 12.95. Found C, 56.82; H, 6.86; N, 5.00; Cl, 12.94.

Example 2. Synthesis of a Morpholine Analogs from Racemic 2-((2-ethoxyphenoxy)methyl)morpholine HCl Scheme II.

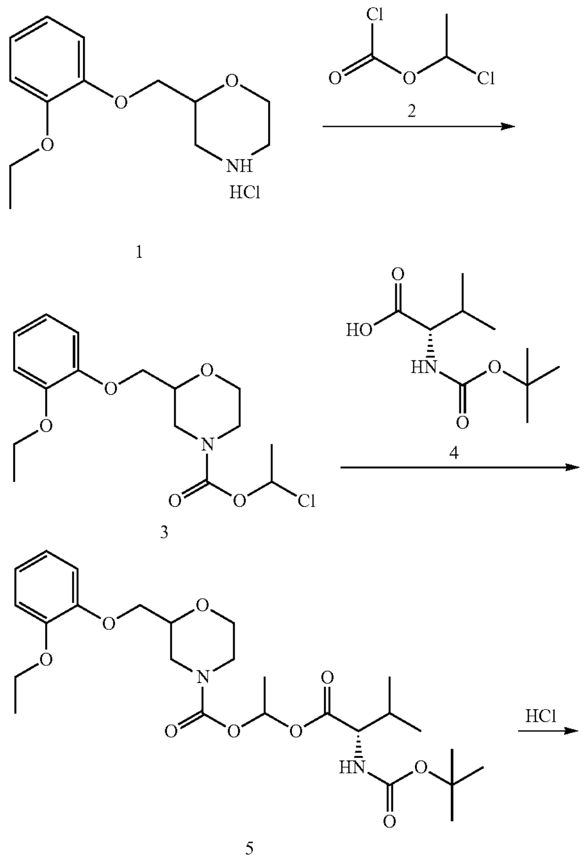

1 2 3 4 5

-continued

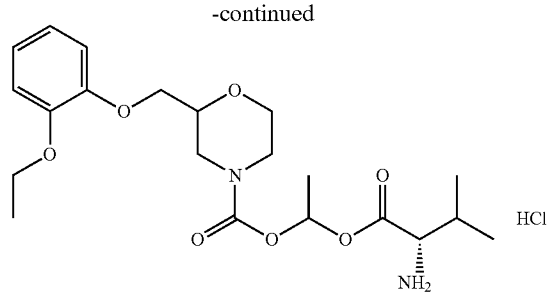

6

The numbering convention for the compounds described in Example 2 below correspond to the compound numbers shown in Scheme II.

In exploratory studies, the process was improved by several novel modifications. These included using the free base of 2-((2-ethoxyphenoxy)methyl)morpholine and diisopropylethylamine as the base catalyst in the first step and using only 1.0 equivalents of the chloroformate 2. The intermediate 3 was isolated by extraction and without using chromatography (avoiding decomposition observed when 3 was chromatographed on silica gel). The condensation of 3 with Boc-L-valine (4) was performed by initial formation of the Cs salt in DMF and carrying out the condensation until intermediate 3 was consumed. The crude 5 was dissolved in ethyl acetate and washed with water and sodium bicarbonate to give the BOC compound 5 as a single spot on TLC and as a single peak on HPLC. Treatment of the ethyl acetate solution of 5 with 2N HCl in dioxane gave the product HCl salt 6. In the exploratory study, a portion of the product was isolated as white solid by filtration of the crude suspension in ethyl acetate/dioxane in an overall yield of 34% (compared to yield of 22% yield as reported in U.S. Provisional Application Ser. No. 63/162,671) along with a syrupy liquid mother liquor that was about 80% pure 6.

Initial scale-up was performed using the process described in four batches to give a total of 57 g of the solid HCl salt 6.

The sample was checked to assess if the scale-up synthesis had affected the ratio of diastereoisomers. Thus a portion of the material 6 was hydrolyzed with 1N NaOH to convert it to 2-((2-ethoxyphenoxy)methyl)morpholine free base and this was converted to the HCl salt. This sample of 2-((2-ethoxyphenoxy)methyl)morpholine HCl obtained from the prodrug showed an optical rotation of $[\alpha]_D^{21}$=+1.75° indicating a predominance for the R-enantiomer of 2-((2-ethoxyphenoxy)methyl)morpholine HCl (literaturel value+4.3°). Since the value was not zero, clearly the solid 6 had a predominance of one isomer and that would be the R-isomer.

Experimental Details

Step 1. 1-Chloroethyl 2-[(o-ethoxyphenoxy)methyl]-4-morpholinecarboxylate (3).

2-((2-ethoxyphenoxy)methyl)morpholine HCl (1·HCl, 32.8 g, 120 mmol) was suspended in 50 mL of water and stirred at 0° C. A solution of 9.6 g of NaOH dissolved in 100 mL of water was added in portions while keeping the solution at 0° C. over 30 min; the solution was kept stirring for an additional 1.5 hr. The mixture was extracted with 4×100 mL of dichloromethane. The combined extract was washed with brine, dried over magnesium sulfate, and evaporated on a rotary evaporator, then kept on a vacuum pump overnight. A colorless oil (28.51 g) of 2-((2-ethoxyphenoxy)methyl)morpholine free base (1) was obtained (theory 28.47 g).

The 2-((2-ethoxyphenoxy)methyl)morpholine base 1 (120 mmol) was dissolved in 200 mL of dichloromethane and stirred at 0° C. (some not fully dissolved). To the solution was added 41.8 mL (240 mmol) of diisopropylethylamine, giving a clear yellow solution. To the solution was added a solution of 18.16 g (122 mmol) of 1-chloroethylchloroformate 2 in 20 mL of dichloromethane over 15 min. The solution was allowed to stir and warm to room temperature over 1.5 hr then to stir at room temperature for 30 min. Water (100 mL) was added and the mixture was extracted twice with dichloromethane. The extract was washed twice with brine, and twice with 2N HCl (confirming the pH of the aqueous phase was pH 2), then again with brine, bicarbonate, brine. The extract was dried over magnesium sulfate and the solvent was evaporated on a rotary evaporator then on high vacuum for 2 hr. A yellow oil (42.81 g) of chloroethylcarbamate 3 was obtained (theory=41.26 g).

Step 2. 1-[(S)-2-(tert-Butoxycarbonylamino)-3-methylbutyroxy]ethyl (S)-2-[(o-ethoxyphenoxy)methyl]-4-morpholinecarboxylate (5).

To a solution of 39.63 g (183 mmol) of L-BOC-valine-OH (4) in 100 mL of DMF was added 29.32 g (90 mmol) of cesium carbonate. The solution was stirred at room temperature for 30 min then the crude chloroethylcarbamate 3 (42.81 g) from above in 50 mL of DMF was added. The mixture was stirred and heated at 80° C. for 1 hr (until TLC showed no 5 remaining. The solution was cooled to room temperature and treated with 100 mL of water plus 50 mL of brine and was extracted with ethyl acetate (4×). The extract was washed successively with sodium bicarbonate (2×), brine, 1N HCl, brine, sodium bicarbonate, and brine (2×), then dried over magnesium sulfate. Norit was added and the mixture was filtered through celite and evaporated to give 63.95 g of the crude BOC product 5 as a yellow oil (theory=62.95 g).

Step 3. 1-[(S)-2-Amino-3-methylbutyroxy]ethyl (S)-2-[(o-ethoxyphenoxy)methyl]-4-morpholinecarboxylate, hydrochloride (6).

The BOC product 5 (63.95 g) from above was dissolved in 110 mL of ethyl acetate and 110 mL of 4N HCl in dioxane was added. A brown solution formed and was stirred for 3 hr at room temperature whereupon a large quantity of a solid formed. The mixture was filtered and the solid washed with ethyl acetate and cold 1:1 ethyl acetate:hexane. The white solid product was dried under vacuum to give 18.45 g (first crop). The mother liquor (40.7 g) was obtained as a brown oil. This was dissolved in 50 mL of ethyl acetate and kept at room temperature overnight, then for 2 days in a freezer. A second crop of 2.3 g was obtained by filtration as before. The solid materials were a single peak on HPLC (fast method (10-70% $CH_3CN$/0.075% TFA/$H_2O$) 15 min). The mother liquor showed the same major peak plus about 10% of 2-((2-ethoxyphenoxy)methyl)morpholine. The HPLC was repeated using a slow method (10-40% $CH_3CN$/0.075% TFA/$H_2O$) 40 min. Under these conditions, the solid was 98% of one component (peak 1) and 2% of a later eluting component (peak 2). The mother liquor showed about a 4:1 ratio of peak 2 to peak 1, indicating that the two peaks were different diastereomers. This was established as a result of the "resolution" at the 2-((2-ethoxyphenoxy)methyl)morpholine center by the L-valine.

The process was repeated. The mother liquor materials were combined. A 15-g portion of the mother liquor material (a syrupy liquid) was subjected to a water-acid-base extraction by dissolving the mother liquor in 50 mL of ethyl acetate and washing with water then with 1N HCl (2×). The ethyl acetate layer contained 2-((2-ethoxyphenoxy)methyl) morpholine, unreacted BOC compound 5, and a trace of the desired compound. The HCl solution was mainly the desired amine 6 HCl salt plus some 2-((2-ethoxyphenoxy)methyl) morpholine and a minor impurity. This solution was made alkaline with sodium bicarbonate, extracted with dichloromethane (3×) washed with brine, and dried over magnesium sulfate. The material was found to be the free base of the desired compound 6 plus ca. 5% of 2-((2-ethoxyphenoxy)methyl)morpholine. The material was kept at room temperature overnight whereupon it decomposed.

A second 15 g portion was treated similarly but without the conversion to the free base. The ethyl acetate phase contained most of the impurities and little product. The HCl solution was extracted with dichloromethane giving mainly the desired HCl salt 6 product (peak 2) plus 4% of 2-((2-ethoxyphenoxy)methyl)morpholine. The aqueous phase contained mainly 2-((2-ethoxyphenoxy)methyl)morpholine.

The remaining 30 g of mother liquor was dissolved in 100 mL of ethyl acetate and extracted 3×1N HCl. The aqueous HCl extract was then rewashed with 2× ethyl acetate (100 mL) and the aqueous HCl phase was then extracted into dichloromethane (3×100 mL). The dichloromethane extract was washed with 50 mL of 1N HCl and that solution was re-extracted with dichloromethane. The combined dichloromethane extracts were dried over magnesium sulfate (sodium), treated with Norit, filtered, and evaporated to give 24.29 g (34 g) of the peak 2 product 6·HCl as a brown oil. This material was treated again in the same manner, affording a total of 22.5 g of product 6·HCl (98.6% product (isomer peak ratio 91.1:8.9) containing 1.4% 2-((2-ethoxyphenoxy)methyl)morpholine.

A similar process was used on 42 g of mother liquor from a different run. This process used only one HCl treatment but more solvents. In that variant, 42 g of mother liquor was dissolved in 300 mL of ethyl acetate and extracted with 2×200 mL of 1N HCl. The aqueous HCl extract was then extracted with 2×250 mL and 1×100 mL of dichloromethane. The combined methylene chloride extracts were washed with 100 mL of 1N HCl, dried over sodium sulfate, and evaporated to give 34 g of the peak 2 product as a brown oil. The isomer peak ratio was 85.7:13.3 plus 3.3% 2-((2-ethoxyphenoxy)methyl)morpholine. LC-MS: $C_{21}H_{32}N_2O_7$ $[M+H]^+$: 425.

Step 4. Preparation of (S)-2-((2-ethoxyphenoxy)methyl) morpholine from the racemate Racemic 2-2-((2-ethoxyphenoxy)methyl)morpholine HCl was chromatographed via supercritical fluid chromatography isolating the (S)-isomer as the slower eluting peak. The preparative separation method was carried out on a Thar 350 preparative SFC (SFC-23) with a ChiralCel column OD, 300×50 mm I.D., 10 μm with a mobile phase A for $CO_2$ and B for Ethanol(0.1% NH3H2O) at a gradient: B 30% and flow rate: 200 mL/min with 100 bar back pressure. Analytical HPLC was performed on Waters UPC2 analytical SFC (SFC-H)/ChiralPak IC, 150×4.6 mm I.D., 3 μm/Mobile phase: A for $CO_2$ and B for Ethanol (0.05% DEA)/Gradient: B 5-40%/Flow rate: 2.5 mL/min/Back pressure: 100 bar/ Column temperature: 35° C./Wavelength: 220 nm. The (S)-isomer was obtained in 99.46% enantiomeric excess. In a subsequent process, the HCl salt was first converted to the free base using ammonium hydroxide to form the free base and extracting it into ethyl acetate, evaporating to an oil and then performing the preparative SFC as above. This produced sharper peaks than via the SFC on the HCl salt.

Example 3. Synthesis of Morpholine Analogs from (S)-2-((2-ethoxyphenoxy)methyl)morpholine HCl Scheme IIIa. Synthesis of 1-[(S)-2-amino-3-methylbutyroxy]ethyl (S)-2-[(o-ethoxyphenoxy)methyl]-4-morpholinecarboxylate.

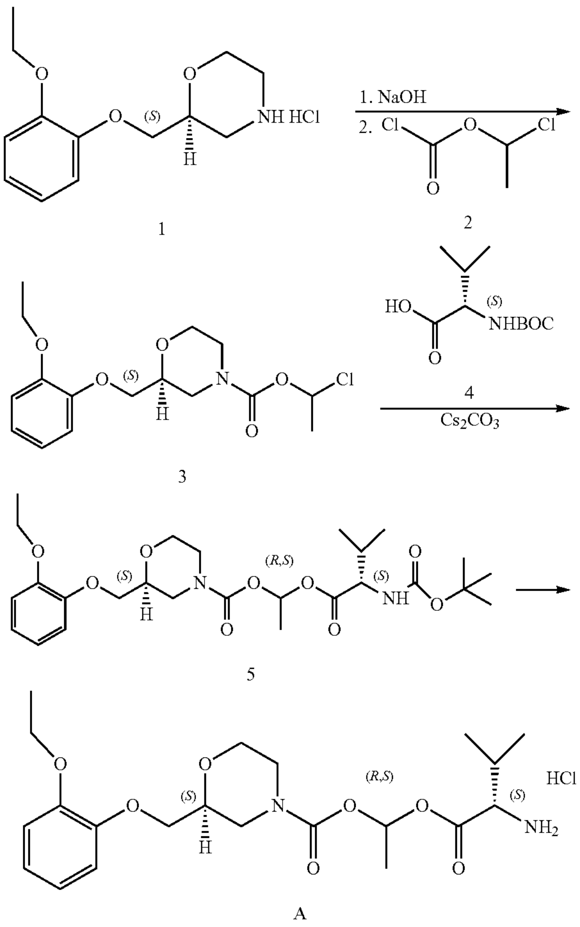

The numbering convention for the compounds described in Step 1 to Step 3 below correspond to the compound numbers shown in Scheme Ma.

Step 1. (S)-1-Chloroethyl 2-[(o-ethoxyphenoxy)methyl]-4-morpholinecarboxylate (3)

(S)-2-((2-ethoxyphenoxy)methyl)morpholine HCl (1, 13.7 g, 50 mmol) was suspended in 50 mL of water and stirred at 0° C. 50 mL of 2N NaOH was added in portions while keeping the solution at 0° C. for 30 min; the solution was kept stirring for an additional 1.5 hr. The mixture was extracted with 4×100 mL of dichloromethane. The combined extract was washed with brine, dried over magnesium sulfate, and evaporated on a rotary evaporator, then kept on a vacuum pump overnight. A colorless oil (11.85 g) of (S)-2-((2-ethoxyphenoxy)methyl)morpholine free base was obtained. The process was repeated on a 100 mmol scale to give an additional 23.7 g (S)-2-((2-ethoxyphenoxy)methyl) morpholine free base. LC-MS: $C_{20}H_{25}NO_3$ $[M+Na]^+$: 328.

(S)-2-((2-Ethoxyphenoxy)methyl)morpholine (50 mmol) was mixed with 100 mL of dichloromethane and stirred at 0°

C. (some not fully dissolved). To the solution was added 17.5 mL (100 mmol) of diisopropylethylamine, giving a clear yellow solution. To the solution was added a solution of 7.15 g (50 mmol) of 1-chloroethylchloroformate 2 in 10 mL of dichloromethane over 15 min. The solution was allowed to stir and warm to room temperature over 1.5 hr then to stir at room temperature for 30 min. Water (100 mL) was added and the mixture was extracted twice with dichloromethane. The extract was washed twice with brine, and twice with 2N HCl (confirming the pH of the aqueous phase was pH 2), then again with brine, bicarbonate, brine. The extract was dried over magnesium sulfate and the solvent was evaporated on a rotary evaporator then on high vacuum for 2 hr. A yellow oil (17.15 g) of chloroethylcarbamate 3 was obtained. The process was repeated on a 100 mmol scale to give an additional 34.3 g of the chloro compound 3. LC-MS: $C_{16}H_{22}ClNNaO_5$ $[M+Na]^+$: 366.

Step 2. 1-[(S)-2-(tert-Butoxycarbonylamino)-3-methylbutyroxy]ethyl (S)-2-[(o-ethoxyphenoxy)methyl]-4-morpholinecarboxylate(5).

To a solution of 16.27 g (75 mmol) of L-BOC-valine-OH (4) in 75 mL of DMF was added 12.2 g (37.5 mmol) of cesium carbonate. The solution was stirred at room temperature for 30 min then 17.15 g of the crude chloroethylcarbamate 3 (50 mmol) from above in 25 mL of DMF was added. The mixture was stirred and heated at 80° C. for 1 hr (until TLC showed no 5 remaining. The solution was cooled to room temperature and treated with 100 mL of water plus 50 mL of brine and was extracted with ethyl acetate (4×). The extract was washed successively with sodium bicarbonate (2×), brine, 1N HCl, brine, sodium bicarbonate, and brine (2×), then dried over magnesium sulfate. Norit was added and the mixture was filtered through Celite and evaporated to give 26.2 g of the crude BOC product 5 as a yellow oil. The process was repeated on a 100 mmol scale to give an additional 52.4 g of the crude BOC compound 5. LC-MS: $C_{26}H_{40}N_2NaO_9$ $[M+Na]^+$: 547.

Step 3. [(5)-1-Amino-2-methylbutoxy]methylmethyl 2-[(o-ethoxyphenoxy)-methyl]-4-morpholinecarboxylate, hydrochloride (A).

The BOC product 5 (26.2 g, 50 mmol) from above was dissolved in 60 mL of ethyl acetate and 50 mL of 4N HCl in dioxane (200 mmol) was added. A brown solution formed and was stirred for 3 hr at room temperature to give 23 g of crude HCl salt. The procedure was repeated on 100 mmol scale to give an additional 46 g of crude salt. The two batches were combined and suspended in 1000 mL of ethyl acetate. The solid which formed was filtered off and dried (32 g). This solid (MS M+H 425) was established to be one diastereomer of the product. The ethyl acetate filtrate was concentrated to 400 mL volume and extracted with 2×250 mL of 1 N HCl. The HCl layer (500 mL) was extracted with 2×300 mL dichloromethane and the combined extract was dried over $Na_2SO_4$ and evaporated to give 32 g of a viscous oil (MS M+H 425). The oil and the solid were combined and dissolved in a mixture of 150 mL of acetonitrile and 250 mL of water, treated with Norit, filtered through Celite and lyophilized to give 61.5 g of compound A as an off-white sticky solid (HPLC purity, 100%). LC-MS: $C_{21}H_{32}N_2O_7$ $[M+H]^+$: 425.

Scheme IIIb. Synthesis of 1-[(S)-2-Amino-3-methylbutyroxy]-2-methylpropyl (S)-2-[(o-ethoxyphenoxy)methyl]-4-morpholinecarboxylate (compound B) and 1-[(R)-2-Amino-3-methylbutyroxy]-2-methylpropyl (S)-2-[(o-ethoxyphenoxy)methyl]-4-morpholinecarboxylate (compound C) from (S)-2-((2-ethoxyphenoxy)methyl)morpholine HCl

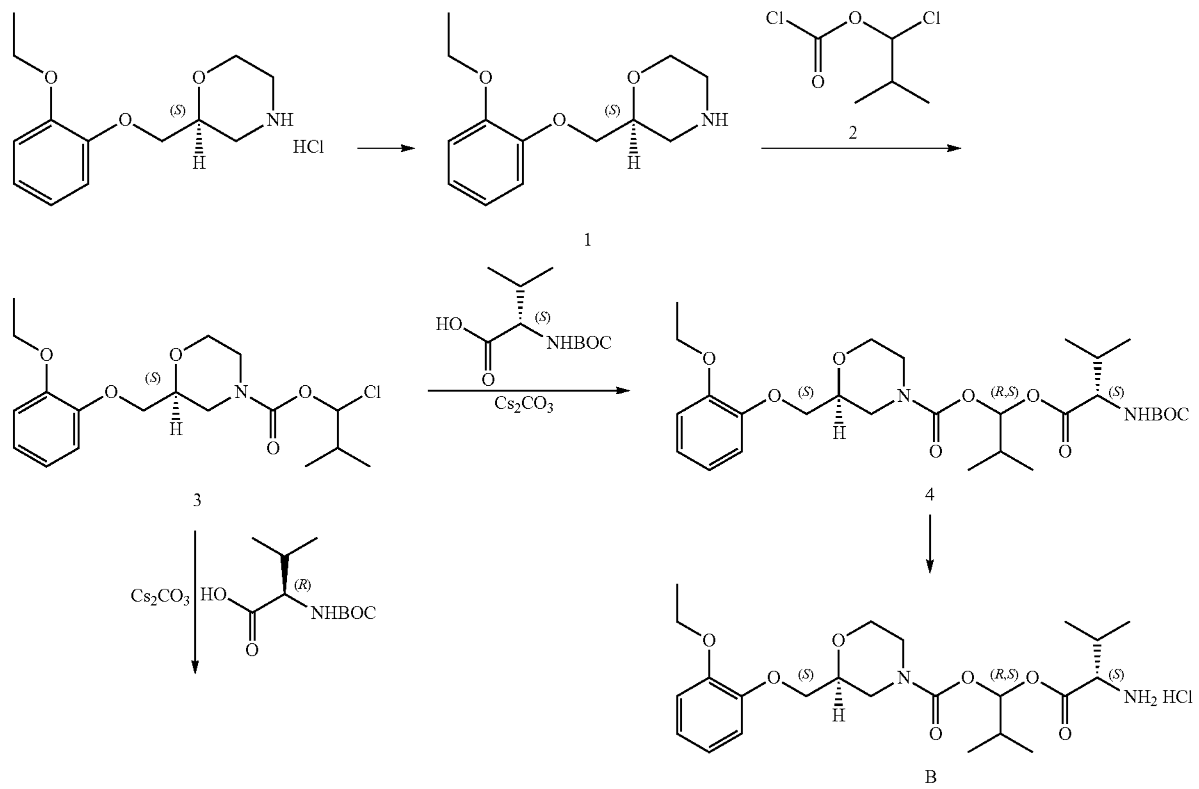

1
3
4
B

-continued

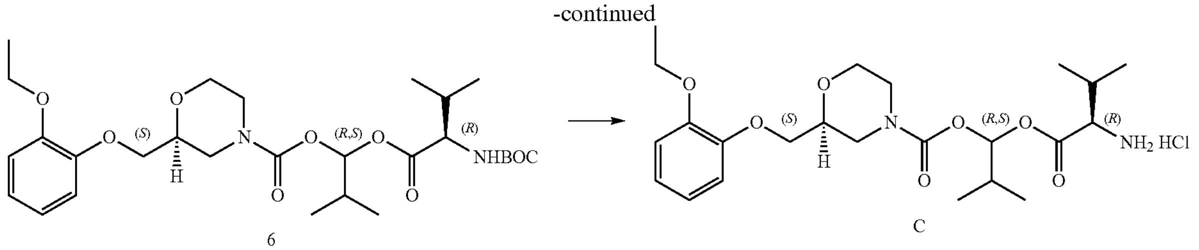

6 C

The numbering convention for the compounds described below correspond to the compound numbers shown in Scheme IIIb.

1-[(S)-2-Amino-3-methylbutyroxy]-2-methylpropyl (S)-2-[(o-ethoxyphenoxy)methyl]-4-morpholinecarboxylate (compound B)

The process to prepare 1-[(S)-2-Amino-3-methylbutyroxy]-2-methylpropyl (S)-2-[(o-ethoxyphenoxy)methyl]-4-morpholinecarboxylate (compound B) is analogous to that for [(S)-1-Amino-2-methylbutoxy]methylmethyl 2-[(o-ethoxyphenoxy)-methyl]-4-morpholinecarboxylate, hydrochloride (compound A) except for the use of the 1-chloro-2-methylpropylchloroformate in place of 1-chloroethylchloroformate.

The method described above for the preparation of (S)-2-((2-ethoxyphenoxy)methyl)morpholine free base was employed in two batches starting with 50 mmol and 100 mmol of (S)-2-((2-ethoxyphenoxy)methyl)morpholine HCl (SFC separation, 99.3% S).

Step 1. (S)-2-Methyl-1-chloroethyl 2-[(o-ethoxyphenoxy) methyl]-4-morpholinecarboxylate (3; Scheme II)

The condensation of 2-((2-ethoxyphenoxy)methyl)morpholine with 1-chloro-2-methylpropylchloroformate (2) was performed on 53 and 100 mmol scales to give 21 g and 42 g of product 3, respectively.

Synthesis of 1-[(R)-2-(tert-Butoxycarbonylamino)-3-methylbutyroxy]-2-methylpropyl (S)-2-[(o-ethoxyphenoxy) methyl]-4-morpholinecarboxylate (4)

16.51 g of BOC-L-Val-OH (76 mmol) and 12.22 g (37.5 mmol) of cesium carbonate ($Cs_2CO_3$) were stirred in 50 mL of DMF for 30 min at RT. To the suspension was added the 50 mmol of the chlorocarbamate 3 in 20 mL of DMF and the mixture was heated in an 80° C. oil bath under $N_2$ for 1.5 hr. After cooling to room temperature, 100 mL of water was added and the mixture was extracted with 4×ethyl acetate, The combined extracts were washed successively with brine, 2×$NaHCO_3$, brine, 1N HCl, brine, $NaHCO_3$ and brine, then dried over $MgSO_4$ and evaporated to give the 31.8 g of 1-[(R)-2-(tert-Butoxycarbonylamino)-3-methylbutyroxy]-2-methylpropyl (S)-2-[(o-ethoxyphenoxy)methyl]-4-morpholinecarboxylate (4) as a light yellow oil.

Synthesis of 1-[(S)-2-Amino-3-methylbutyroxy]-2-methylpropyl (S)-2-[(o-ethoxyphenoxy)methyl]-4-morpholinecarboxylate(compound B)

To a solution of 31.8 g 1-[S)-2-(tert-Butoxycarbonylamino)-3-methylbutyroxy]-2-methylpropyl (S)-2-[(o-ethoxyphenoxy)methyl]-4-morpholinecarboxylate (4) in 60 mL of ethyl acetate was added 60 mL of 4N HCl in dioxane. The solution was stirred at room temperature for 4 hr then the solvent was evaporated to give 29 g of 1-[(S)-2-Amino-3-methylbutyroxy]-2-methylpropyl (S)-2-[(o-ethoxyphenoxy)methyl]-4-morpholinecarboxylate hydrochloride (compound B) as a yellow oil.

The previous two reactions were repeated on 100 mmol scale to give another 59 g of compound B as a yellow oil. The batches were combined and dissolved in 400 mL of ethyl acetate. Hexane (300 mL) was then added and the solution extracted with 2×400 mL and 2×300 mL of 1N HCl. The organic phase was discarded and the aqueous HCl phase was washed with 5×200 mL of 50% ethyl acetate/hexane. The organic phase was discarded and the aqueous HCl phase was extracted with 4×200 mL of dichloromethane. The dichloromethane solution was washed with 100 mL of 1N HCl, dried over $MgSO_4$, and treated with Norit, and evaporated. The oil was dissolved in 140 mL of acetonitrile and 350 mL of water was added, then the solution was lyophilized to give 60.2 g of 1-[(S)-2-amino-3-methylbutyroxy]-2-methylpropyl (S)-2-[(o-ethoxyphenoxy)methyl]-4-morpholinecarboxylate hydrochloride (compound B) as a white solid. (HPLC 98.9%; LC-MS: $C_{23}H_{36}N_2O_7$ $[M+H]^+$: 453). A long elution program resolved the diastereoisomers into two equal peaks.

Synthesis of 1-[(R)-2-Amino-3-methylbutyroxy]-2-methylpropyl (S)-2-[(o-ethoxyphenoxy)methyl]-4-morpholinecarboxylate hydrochloride (compound C)

The process for the synthesis of compound B was repeated except that N-BOC-D-Val was used in the coupling to the chloro compound 3 to give the intermediate 6. Deprotection of 6 on a 100 mmol scale was done using 110 mL of 4N HCl in dioxane in 110 mL of ethyl acetate to give 48.9 g of crude HCl salt. This was combined with the crude HCl salt from a 50 mmol process to give a total of 74 g of crude salt. This was dissolved in 900 mL of 60:40 ethyl acetate:hexane and extracted with 1 L of 1N HCl. The HCl layer was washed with 400 mL of 50:50 ethyl acetate:hexane and then extracted with a total of 2 L of dichloromethane. The dichloromethane extract was dried over $Na_2SO_4$ and evaporated to give 76.88 g of crude 1-((D-valyl)oxy)-2-methylpropyl (2S)-2-((2-ethoxyphenoxy)methyl)morpholine-4-carboxylate (compound C) as the HCl salt. The crude salt (76 g) was dissolved in 200 mL of acetonitrile and 200 mL of water, treated with Norit, filtered through Celite, and lyophilized to give 65.1 g of 1-[(R)-2-Amino-3-methylbutyroxy]-2-methylpropyl (S)-2-[(o-ethoxyphenoxy)methyl]-4-morpholinecarboxylate hydrochloride (compound C) as a white solid. (HPLC 99.81%; LC-MS: $C_{23}H_{36}N_2O_7$ $[M+H]^+$: 453).

Example 4. Synthesis of (S)-4-benzyl-2-((2-ethoxyphenoxy)methyl)morpholine

Scheme IV. Alternate route to synthesize (S)-4 benzyl-2-((2-ethoxyphenoxy)methyl)morpholine (5)

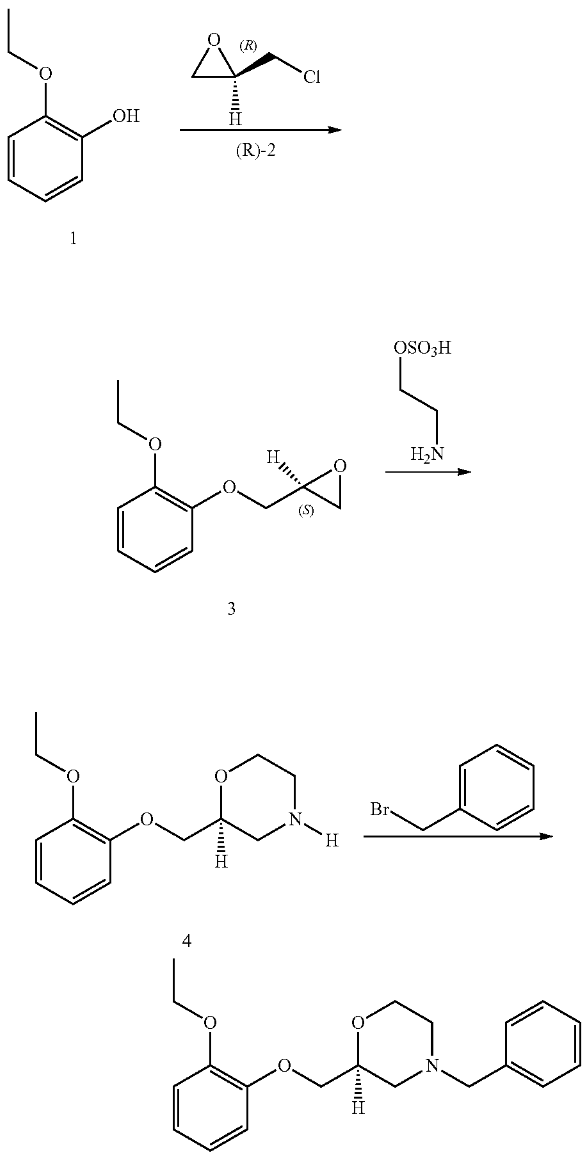

The numbering convention for the compounds described below correspond to the compound numbers shown in Scheme IV.

2-ethoxyphenol 1 is reacted with (R)-epichlorohydrin to give an intermediate epoxide 3 that is then treated with aminoethylsulfate and sodium hydroxide to give (S)-2-((2-ethoxyphenoxy)methyl)morpholine. This process was enantioselective and afforded product that was ca. 92.5% (S).

(S)-4-benzyl-2-((2-ethoxyphenoxy)methyl)morpholine was prepared from (S)-2-((2-ethoxyphenoxy)methyl)morpholine by alkylation with benzyl bromide.

Example 5. Alternate Synthesis of (S)-4-benzyl-2-((2-ethoxyphenoxy)methyl)morpholine Scheme V. Synthesis of (S)-4 benzyl-2-((2-ethoxyphenoxy)methyl)morpholine

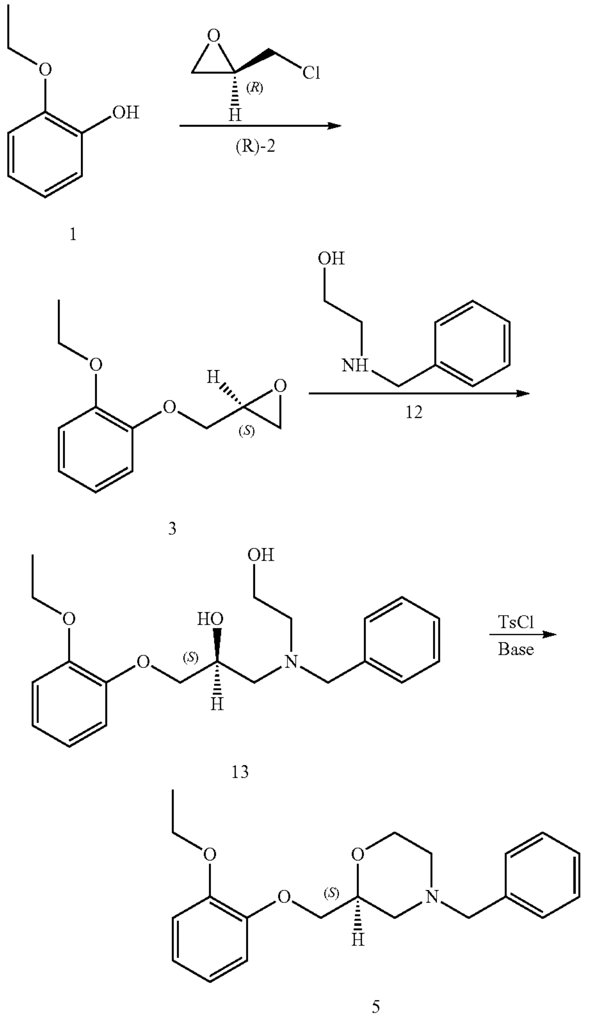

The numbering convention for the compounds described below correspond to the compound numbers shown in Scheme V.

Effort was taken to design a synthesis of (S)-4-benzyl-2-((2-ethoxyphenoxy)methyl)morpholine by a route that does not involve benzylation of (S)-2-((2-ethoxyphenoxy)methyl)morpholine. Several possible routes are precedented based on either S- or racemic 2-((2-ethoxyphenoxy)methyl)morpholine syntheses. In our routes these syntheses use chiral epichlorohydrin as the source of the S-enantiomer. One route that appeared likely to lead to the (S)-2-((2-ethoxyphenoxy)methyl)morpholine is based on the previously disclosed synthesis of racemic 2-((2-ethoxyphenoxy)methyl)morpholine (Liang, Bhatt, et al., U.S. Pat. No. 9,403,783). This process was adapted to give the epoxide intermediate 3 starting from R-epichlorohydrin. This epoxide was used to prepare (S)-2-((2-ethoxyphenoxy)methyl)morpholine via ring opening with aminoethyl hydrogen sulfate and cyclization (U.S. Pat. No. 3,712,890). On that basis, the ring opening of 3 with hydroxyethylbenzylamine (12) is expected to give the same (5)-4-benzyl-2-((2-ethoxyphenoxy)methyl)morpholine via the diol 13.

Example 6. Synthesis of Salts of Morpholine Derivatives from (S)-4-benzyl-2-((2-ethoxyphenoxy)methyl)morpholine Scheme VI.

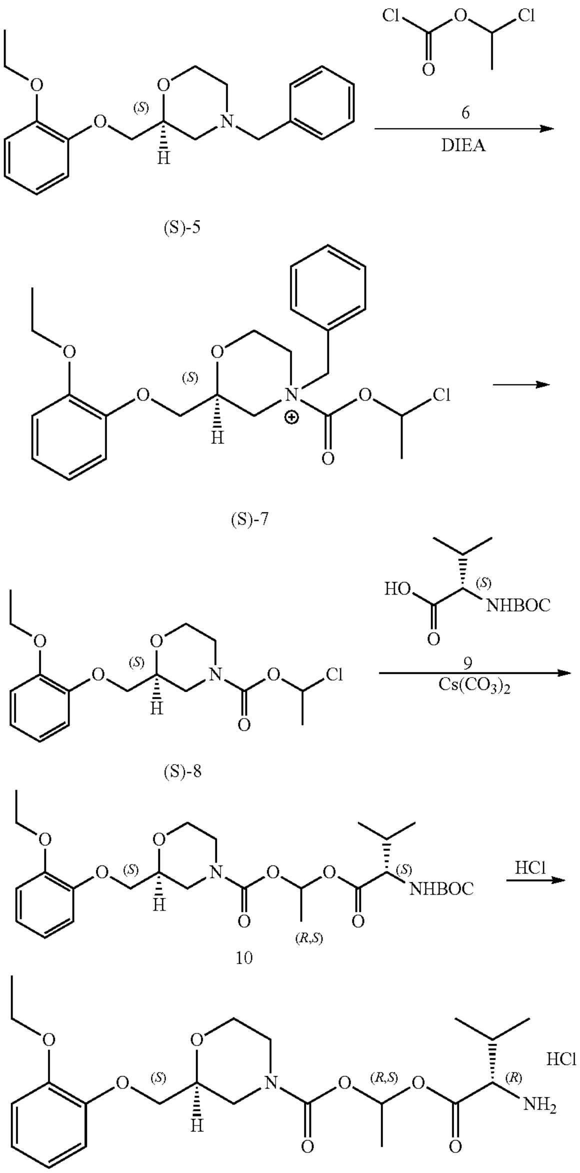

(S)-5

(S)-7

(S)-8

10

11

The numbering convention for the compounds described in Example 6 correspond to the compound numbers shown in Scheme VI.

The (S)-4-benzyl-2-((2-ethoxyphenoxy)methyl)morpholine (5) (3.87 g of the above material, 10 mmol) was dissolved in 25 mL of dichloromethane and stirred in an ice bath. A solution of 1-chloroethylchloroformate 6 (1.88 g, 13.2 mmol) in 5 mL of dichloromethane was added over ca. 2 min and kept at ca. 3° C. for 90 min then allowed to warm to room temperature and stir for 1 hr. The reaction mixture was diluted with dichloromethane (100 mL) and washed with water (50 mL), 1N HCl (50 mL), Bicarbonate (50 mL) and brine (50 mL), dried over sodium sulfate, then evaporated on the rotary evaporator and then overnight on a vacuum pump. The residue was dissolved in acetonitrile (50 mL) and washed with hexane (3×100 mL) to remove remaining amounts of benzyl chloride byproduct from the debenzylation via 7. The acetonitrile layer was concentrated to give 3.47 g of the chlorocarbamate 8.

N-Boc-L-valine 9 (3.47 g; 16 mmol and cesium carbonate (2.6 mg; 8 mmol) were stirred in 20 mL of DMF for 30 min. To the mixture was added a solution of the chlorocarbamate 8 from Step 2 (3.43 g, 10 mmol) in 20 mL of DMF and the mixture was stirred and heated at 85° C. for 1 hr. After cooling to room temperature, the mixture was extracted with ethyl acetate (100 mL). The ethyl acetate solution was washed with water (2×100 mL), bicarbonate (75 mL), 1N HCl (2×100 mL), and brine (50 mL) and dried over sodium sulfate. The solvents were evaporated to give the crude Boc-protected compound 10 (5.8 g) as a syrup.

The total Boc protected compound 10 from Step 3 (5.8 g; 10 mmol) was dissolved in ethyl acetate (25 mL) and 4N HCl in dioxane (11 mL, 44 mmol) was added. The mixture was stirred for 4 hr at room temperature then concentrated under vacuum. The crude compound was dissolved in ethyl acetate (50 mL) and extracted with 1N HCl (2×70 mL). The HCl layer was extracted with dichloromethane (1×100 mL; 1×50 mL). HPLC of a sample of the extract showed purity of 96.6%. The dichloromethane layer was washed with 1N HCl (80 mL) then dried over sodium sulfate and evaporated. After drying under vacuum at room temperature overnight, the 1-[(S)-2-Amino-3-methylbutyroxy]ethyl (S)-2-[(o-ethoxyphenoxy)methyl]-4-morpholinecarboxylate HCl product (11, 3.65 g) was obtained as a pale yellow foam. This final process gave 1-[(S)-2-Amino-3-methylbutyroxy]ethyl (S)-2-[(o-ethoxyphenoxy)methyl]-4-morpholinecarboxylate HCl (11) with no unreacted (S)-4-benzyl-2-((2-ethoxyphenoxy)methyl)morpholine and lacking the byproduct of reaction of the byproduct benzyl chloride with N-Boc-L-lysine (9). This resulted in product with improved purity (99.15% vs. 96.6%). Based on 10 mmol of (S)-4-benzyl-2-((2-ethoxyphenoxy)methyl)morpholine used, the 3.65 g of 1-[(S)-2-Amino-3-methylbutyroxy]ethyl (S)-2-[(o-ethoxyphenoxy)methyl]-4-morpholinecarboxylate HCl salt (11) represents an overall yield of 79.2%. LC-MS: $C_{21}H_{32}N_2O_7$ $[M+H]^+425$. The product 1-[(S)-2-Amino-3-methylbutyroxy]ethyl (S)-2-[(o-ethoxyphenoxy)methyl]-4-morpholinecarboxylate (11) is a 1:1 mixture of diastereomers at the acetal center. One of the isomers (faster eluting on reverse phase HPLC) can be easily obtained as a solid and could be recrystallized to provide material of high purity from ethanol/MTBE or ethyl acetate with a recovery of ca. 85% of the theoretical amount. Further work showed that the solid HCl salt could be recrystallized from isopropanol to give fine needles of crystals. The liquid, slower eluting isomer could not be crystallized as the HCl salt under multiple trials with different solvent systems. It appears that the two diastereoisomers may have different conformations that favor crystallization of the faster eluting one. The recrystallized HCl salt forms needles that appear to be too fine for X-ray structure determination. Further crystallization attempts may be warranted to see if suitable crystals may be obtained to determine if this isomer has the S,S,S or S,R,S configuration.

Salts of Morpholine Derivatives

Experiments on exchanging the HCl salt for alternative acids were also completed. The previous experience in isolating the free base by treatment of the HCl salt with 1N NaOH had failed due to hydrolysis by the strong base to give 2-((2-ethoxyphenoxy)methyl)morpholine. However, it was found that the HCl salt in solution in ethyl acetate or dichloromethane could be washed with saturated sodium bicarbonate and brine, and dried over sodium or magnesium sulfate to give solutions of the free base that remained stable. The free base solutions could then be treated with 1 equivalent of different acids to form other salts. Salts with maleic acid, citric acid, and p-toluenesulfonic acid and methanesulfonic acid were generated from the mixed diastereomeric HCl salts but could not be recrystallized. A potential alternative approach involved first separating the solid diastereomer of the HCl salt by crystallization from ethyl acetate and isolation of the liquid diastereomer from the mother liquor to enable evaluations of various salts of each diastereomer separately. Converting these isomers separately to the free base and then to the p-toluenesulfonates gave both as crystalline solids. Attempts to crystallize the isomer mixture of tosylates were not successful. Overall it would appear that the tosylates of the individual diastereoisomers can be prepared and crystallized then blended 1:1 to give a suitable product.

Synthesis of Salts 1.152 g (2.5 mmol) of the mixed diastereomeric HCl salts was dissolved (readily) in 5 mL of ethyl acetate and seeded with crystals reserved from earlier studies. After 1 hr the solution was concentrated to a volume of 3 mL and allowed to stand at room temperature overnight, forming a thick paste of crystalline solid. Ethyl acetate (3 mL was added and the solid collected by filtration and rinsed with 1 mL of ethyl acetate. After drying on a vacuum pump, 487 mg of the HCl salt was obtained in the first crop (84.5% of theoretical). The mother liquor was evaporated and the gummy residue (593.9 mg) was dissolved in 3 mL of ethyl acetate and diluted with 3 mL of MTBE. The solution was allowed to stand at room temperature overnight, but no solid was obtained.

The mixture of diastereoisomers of the HCl salt (1.15 g, 2 mmol) was dissolved in 3.5 mL of ethyl acetate and seeded. Crystals formed within 1 hr and the solvent was removed by pipette and the solid rinsed with 5 mL of 1:1 ethyl acetate:hexane and dried to give 562.2 mg of the solid isomer. The solid was recrystallized from isopropanol 3.5 mL overnight giving fine needles. The mother liquor was evaporated to a thick syrup, dissolved in 1 mL ethyl acetate and diluted with 1.5-2 mL of hexane. After standing at room temperature for 30 min an oil separated, so an additional 0.5 mL of ethyl acetate was added and the mixture was warmed to dissolve and allowed to stand overnight. Additional solid was obtained but HPLC showed that it was only a second crop of the faster eluting isomer and the mother liquor was only the liquid, slower eluting isomer.

Isolation of free base from liquid HCl salt isomer. The solvents from the mother liquors from crystallization of the HCl salt (2.5 mmol scale) were evaporated and the residue dissolved in 6 mL of dichloromethane and the solution washed 2×bicarbonate.

Mesylate Formation

The dichloromethane solution of free base derived from 593.9 mg (1.29 mmol) of the liquid HCl isomer mother liquor was then treated with 1.5 mL of 1N methanesulfonic acid in methanol. The solution was diluted with 2 mL of dichloromethane and washed 1×3 mL of water. The solvent was evaporated and some salts precipitated so the mixture was redissolved in dichloromethane, dried over magnesium sulfate and dried. The residue was dissolved in ethyl acetate (2 mL) and MTBE (2 mL) but no solid formed. The solvents were removed (and using 5 mL of toluene to dry the material further). This was then dissolved in isopropanol (0.5 mL) and allowed to stand overnight (no solid). The material was dissolved in ethyl acetate and converted again to the free base with bicarbonate then washed with brine, and dried over magnesium sulfate.

Maleate Formation

The ethyl acetate solution of the free base was treated with a solution of 150 mg of maleic acid in 2 mL of isopropanol. The solvent was evaporated (thick oil) (TLC using 9:1 dichloromethane:methanol) shows separation of the maleic acid and free base. HPLC shows peaks for maleic acid and the slower eluting isomer, but no 2-((2-ethoxyphenoxy) methyl)morpholine indicating that the maleic acid salt was stable, but again, not crystalline. The material was dissolved in dichloromethane, washed with water, and evaporated to give 374 mg of the maleate as an oil.

Tosylate Formation

In another experiment, the liquid HCl salt isomer (174.7 mg, 412 mmol) was dissolved in 7 mL of ethyl acetate. The solution was washed with bicarbonate (2×5 mL), brine, and dried over magnesium sulfate and evaporated (rotary evaporator with bath <30° C.) and dried under vacuum for 30 min to give the free base. Ethyl acetate (2 mL) was added followed by 78.3 mg of p-toluenesulfonic acid monohydrate in 0.5 mL of ethanol plus 3 mL of ethyl acetate. The solution was concentrated to a volume of 0.5 mL and re-evaporated with 5 mL of ethyl acetate to removed traces of ethanol, giving a sticky foam. The material was dissolved in 2 mL of ethyl acetate and hexane (ca. 2 mL) was added just until cloudy. Upon standing, crystals formed and the mixture was allowed to stand over the weekend to give lots of white crystals. The solvent was removed via pipette and the residue rinsed with 1:1 ethyl acetate:hexane and dried to give 188 mg of the tosylate as a white solid in the first crop.

The above process was repeated starting from solid isomer HCl salt (486 mg, 1.054 mmol) dissolving it in ethyl acetate and washing with sodium bicarbonate, brine, and drying over magnesium sulfate as above. The solution of free base was then treated with p-toluenesulfonic acid monohydrate (200.56 mg, 1.054 mmol), first dissolved in 1 mL of ethanol then diluted with 2 mL of ethyl acetate. The solution was diluted with 1 mL of ethyl acetate and 1 mL of hexane. The solvents were removed to give 487.1 mg of the tosylate as a foamy solid. This was dissolved in 2 mL of ethyl acetate and 2 mL of hexane and allowed to crystallize at room temperature overnight to form crystalline tosylate. The solvent was removed by a pipette and the solid rinsed with 1:1 ethyl acetate: hexane and the solid dried to give 345.8 mg of the solid tosylate. The mother liquor was evaporated to give 187.4 mg of material.

The isomer mixture of the HCl salt (780 mg, 1.692 mmol) was dissolved in 5 mL of ethyl acetate and converted to the free base as above. The free base was dissolved in 5 mL of ethyl acetate and 321.8 mg of p-toluenesulfonic acid monohydrate dissolved in 1 mL of methanol was added. The solution was diluted with 3-4 mL of hexane until partly cloudy and seeds of both pure enantiomers of crystalline tosylate were added. TLC of the mixture of tosylates (9:1 dichloromethane:methanol) showed a slight separation of the isomers with the liquid isomer-derived tosylate running slightly faster than the tosylate from the solid isomer. After standing overnight and trying other solvents (isopropanol, MTBE) no crystals of either diastereomer formed.

Example 7. Definitive Assignment of Chirality of (S)-2-((2-ethoxyphenoxy)methyl)morpholine The scientific literature on 2-((2-ethoxyphenoxy)methyl) morpholine enantiomers indicates that the S-isomer is biologically much more potent than the R-isomer. The assignment of R and S to the enantiomers is linked back to older literature relating the absolute configuration with that of propranolol and established through correlation with S-lactic acid and via some circular dichroism spectroscopy. (Howe, et al., J. Med. Chem., 1976, 19, 1074.) Since the (S)-2-((2-ethoxyphenoxy)methyl)morpholine prodrugs including 1-[(S)-2-Amino-3-methylbutyroxy]ethyl (S)-2-[(o-ethoxyphenoxy)methyl]-4-morpholinecarboxylate are potential drug candidates, we sought to validate the chiral configuration as (S) through X-ray crystallography.

While no X-ray structure of an (S)-2-((2-ethoxyphenoxy) methyl)morpholine salt has never been reported, the racemic material has been crystallized and the X-ray structure determined as its HCl salt (J.Ouhabi, M.Saux, A.Carpy, *Acta Crystallographica, Section C: Crystal Structure Communications,* 1990, 46, 2160. For potential X-ray studies we prepared the tosylate, mesylate, and hydrobromide salts (each salt incorporates heavy atoms to facilitate absolute chirality determination). The crystals obtained from these salts were very fine needles or cottony solids. The best sample (HBr salt, needles) was submitted for X-ray but the needles were too fine for X-ray studies.

Since the 2-((2-ethoxyphenoxy)methyl)morpholine salts were not giving suitable crystals, we prepared a sample of (S)-4-benzyl-2-((2-ethoxyphenoxy)methyl)morpholine produced from pure (S)-2-((2-ethoxyphenoxy)methyl)morpholine that had been obtained from the racemate by chiral SFC (99.3% S). This was treated with 48% HBr in ethanol and evaporated to give a white solid of the HBr salt. Recrystallization of the HBr salt from ethanol afforded large, plate-like crystal forms. These were submitted for X-ray analysis and determined to be suitable for study. The 4-benzyl-2-((2-ethoxyphenoxy)methyl)morpholine HBr crystals were shown to have the (S)-configuration and to have one molecule of water in the crystal. The structure is shown in FIG. 1.

This study confirms all the prior assumptions about the S-isomer of 2-((2-ethoxyphenoxy)methyl)morpholine being the biologically potent isomer. It also confirms that this (S)-isomer is the configuration isolated from the resolution procedure of Howe, et al. and is the same isomer as the slower moving peak on chiral SFC and the isomer separated racemic 2-((2-ethoxyphenoxy)methyl)morpholine to produce large amounts of (S)-2-((2-ethoxyphenoxy)methyl) morpholine for the prodrug studies. Based on these results and the correlations noted above, the configurations of (S)-2-((2-ethoxyphenoxy)methyl)morpholine and (S)-4-benzyl-2-((2-ethoxyphenoxy)methyl)morpholine are confirmed as (S).

Example 8. Novel Chiral Synthesis of Intermediate of Morpholine Derivatives

Scheme VIII. Synthesis of 1-[(S)-2-Amino-3-methylbutyroxy]ethyl (S)-2-[(o-ethoxyphenoxy)methyl]-4-morpholinecarboxylate

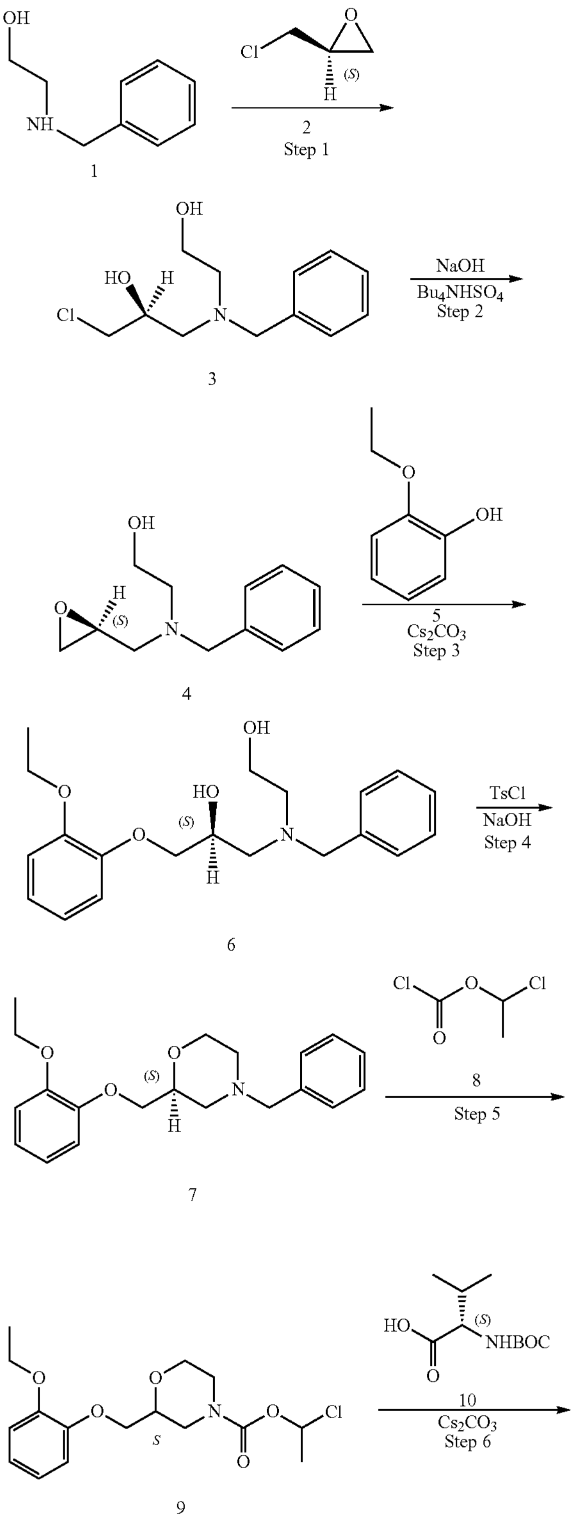

-continued

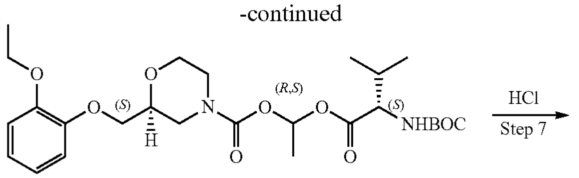

11

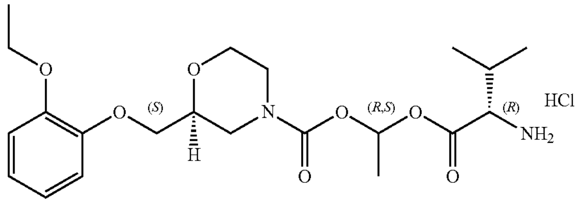

12

The numbering convention for the compounds described in Example 8 correspond to the compound numbers shown in Scheme VIII.

Route to (S)-4-benzyl-2-((2-ethoxyphenoxy)methyl)morpholine

The synthesis of 1-[(S)-2-amino-3-methylbutyroxy]ethyl (S)-2-[(o-ethoxyphenoxy)methyl]-4-morpholinecarboxylate HCl (12) via the new route (Scheme III) proceeds via the N-benzyl ethanolamine (1) opening of (S)-(+)-epichlorohydrin (2, source of chirality) through formation of chlorohydrin 3, epoxide 4, diol 6 and cyclization to (S)-4-benzyl-2-((2-ethoxyphenoxy)methyl)morpholine (7). The route has been scaled up starting with a total of 1.2 mol of the ethanolamine 1. Via the new route, crystallization of the crude (S)-4-benzyl-2-((2-ethoxyphenoxy)methyl)morpholine (7·HCl) under optimized conditions gives >99% of the (9-isomer.

Experimental Details

Step 1: 2-Benzylaminoethanol (1, 90.73 g, 600 mmol) and (S)-(+)-epichlorohydrin (2, 61.06 g, 660 mmol, 1.1 equivalents) were dissolved in 220 ml of methanol, stirred under nitrogen and warmed to 35° C. for 22 hr. The methanol was evaporated and 100 ml of toluene was added and the toluene evaporated. The toluene addition and evaporation was repeated 3 additional times to remove traces of epichlorohydrin and/or methanol and the oil was dried on a vacuum pump for 4 hr. The product chlorohydrin 3 (155 g) was obtained as a light yellow oil. HPLC (5-50-90% $CH_3CN$; $H_2O$/0.075% TFA) showed the main peak at 6.23 min (64% purity).

Figure 2:
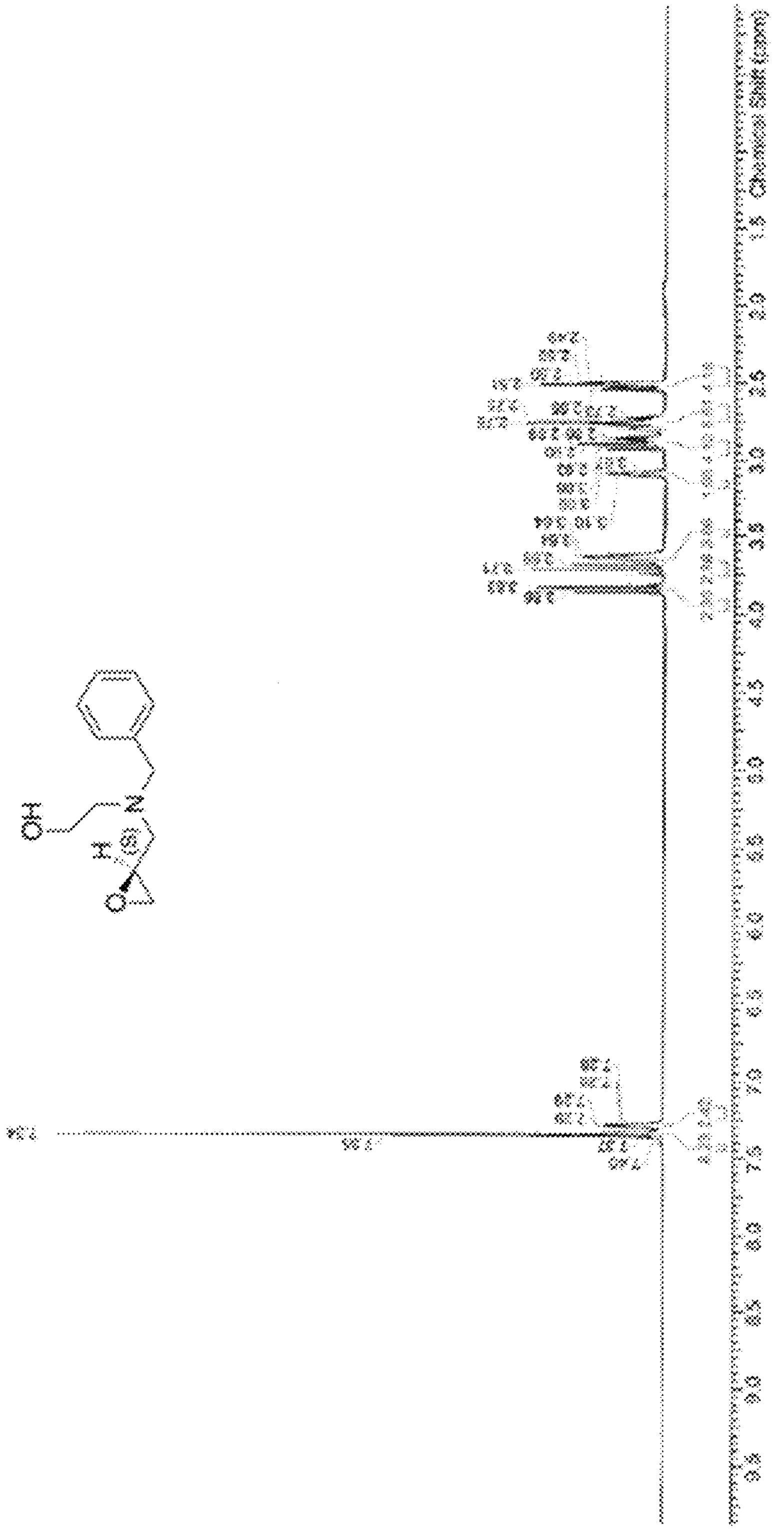
FIG. 2 shows the $^1$H NMR spectrum of compound 4 from Example 8.
Figure 3:
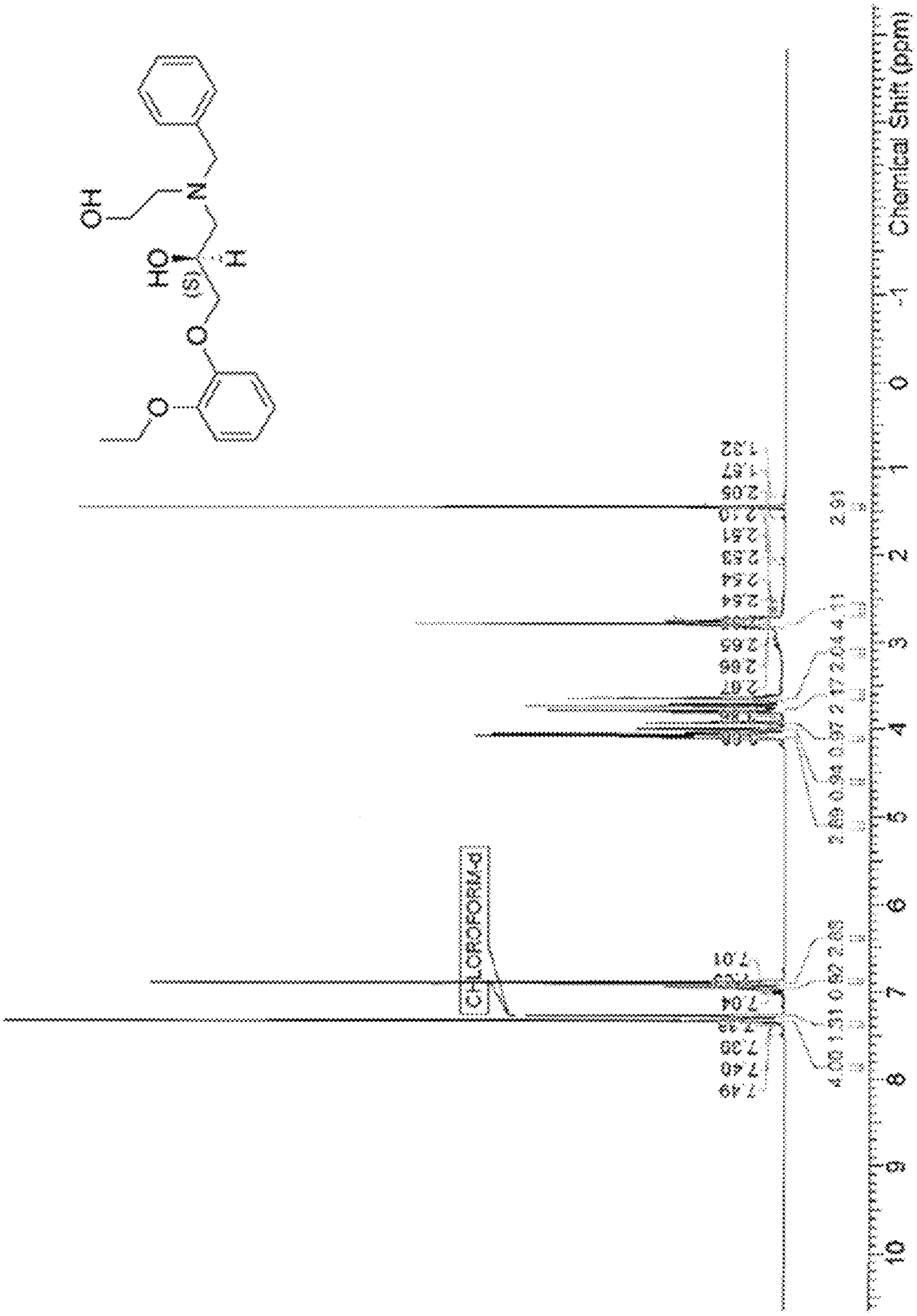
FIG. 3 shows the $^1$H NMR spectrum of compound 6 from Example 8.
Figure 4:
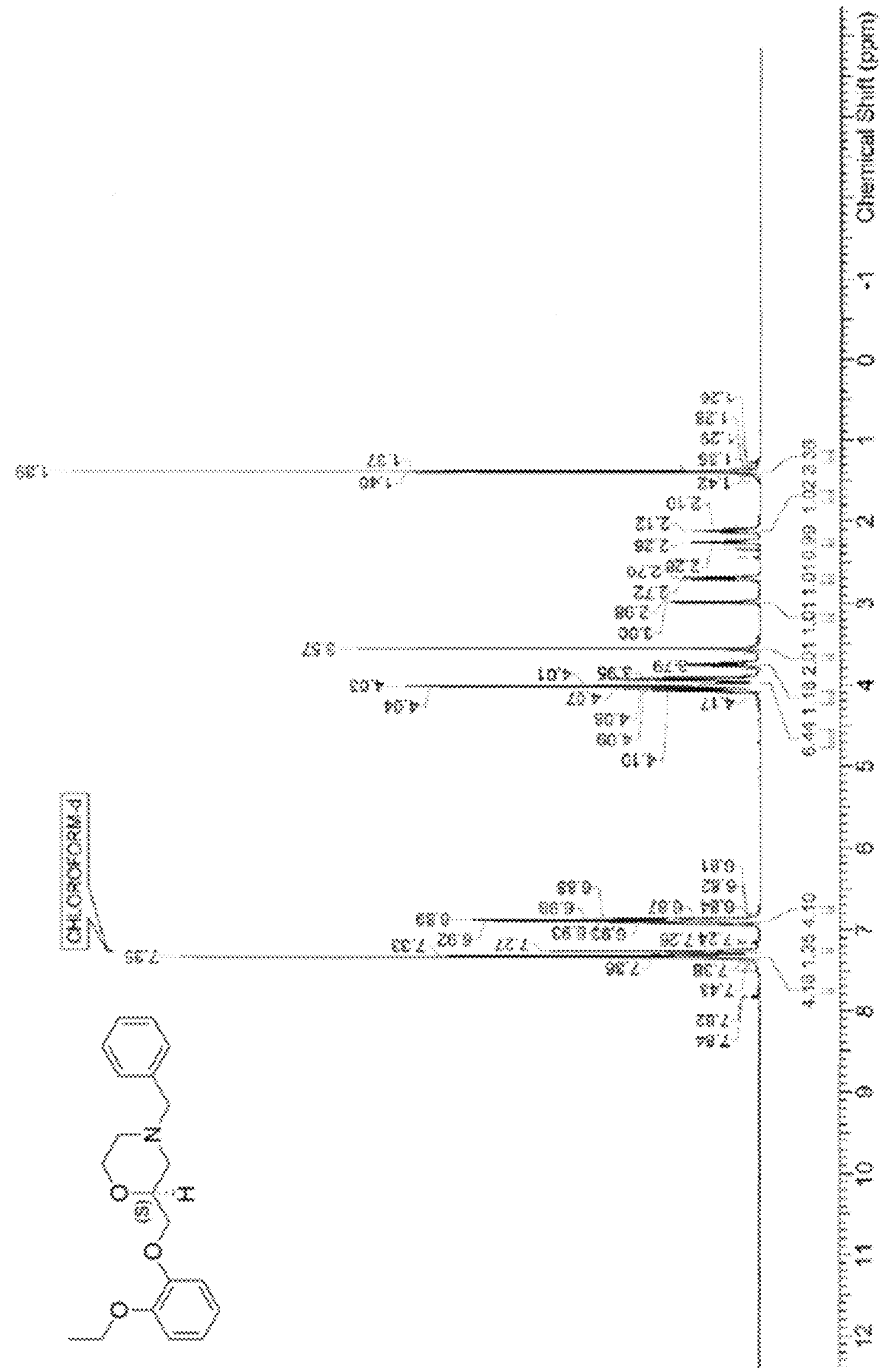
FIG. 4 shows the $^1$H NMR spectrum of compound 7 from Example 8.

Step 2: The crude chlorohydrin 3 (155 g) was dissolved in 300 ml of MTBE. To the solution was added 2.4 g of tetrabutylammonium hydrogen sulfate and a solution of 25.2 g (630 mmol) of sodium hydroxide in 48 ml of water. The mixture was stirred for 1.5 hr at room temperature under nitrogen. The layers were separated and the aqueous layer was extracted with 100 ml of MTBE. The combined extracts were dried over magnesium sulfate and evaporated on a rotary evaporator then dried on high vacuum for 3 hr at room temperature. The epoxide 4 was obtained as a light yellow oil (113 g). HPLC using the same conditions as for 3 showed the product peak for epoxide 4 at 6.74 min (64.3%). LC-MS: $C_{12}H_{17}NO_2$ $[M+H]^+$: 208.17. The $^1H$ NMR spectrum of 4 is shown in FIGS. 2A-2B.

Figure 5:
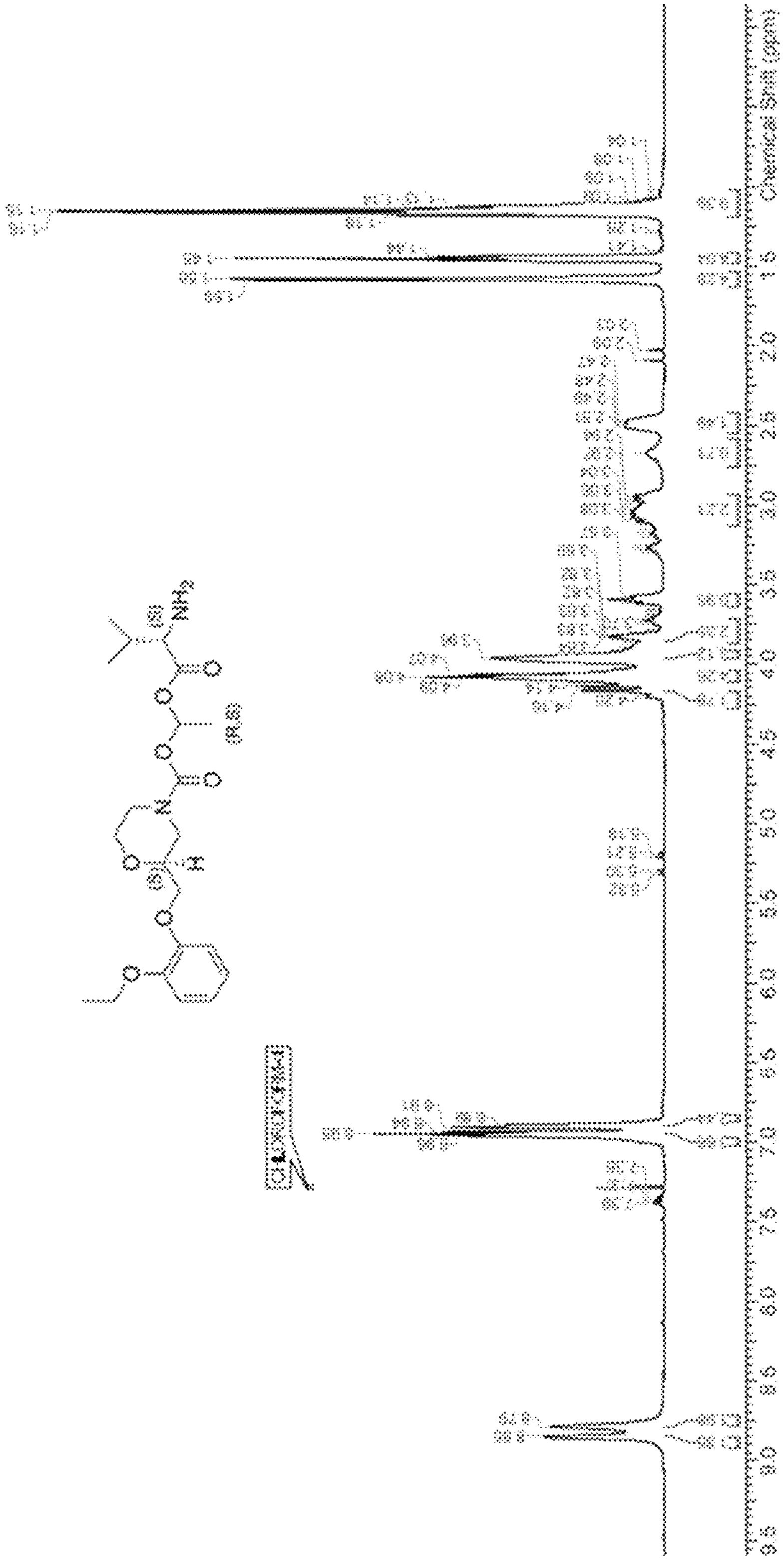
FIG. 5 shows the $^1$H NMR spectrum of compound 12 from Example 8.

Step 3: The epoxide 4 (113 g) and 2-ethoxyphenol (5, 90.4 g, 655 mmol) were dissolved in 450 ml of toluene. The mixture was stirred (mechanical stirrer) and cesium carbonate (106.3 g, 327 mmol) was added in portions over ca. 30 min resulting in a temperature rise from room temperature to 34° C. The mixture was stirred and allowed to cool to 32° C. over 30 min. Then the mixture was heated gradually (heating mantle) raising the internal temperature to 110° C. over a period of 1 hr and kept at 110° C. for 1 hr when all of the epoxide 4 was consumed. The brown mixture was then cooled to room temperature, filtered through Celite, and the toluene evaporated to give a brown oil. The oil was dissolved in 200 ml of dichloromethane and 200 ml of 2N NaOH was added. The mixture stirred for 10 min then extracted with 2×100 ml of dichloromethane and the extracts washed with 2×100 ml of 2N NaOH (to remove unreacted phenol) and 2×brine. To the dichloromethane layer was added 200 ml of brine and 55 ml of conc. HCl was added (until the aqueous layer was pH 3). The mixture was stirred for 10 min, the organic layer was separated and then washed with 2×1N HCl (100 ml saturated with NaCl) (to remove cyclic amine byproducts) then 2× brine. The organic phase was then treated with 2N NaOH until pH >10 and was stirred for 10 min, washed 2× with brine, and dried over magnesium sulfate. Evaporation of the solvent followed by drying on a vacuum pump gave 149 g of diol 6 as a light brown oil. HPLC using the 50-90% gradient as before showed the main peak for diol 6 at 14.48 min; using a 10-70-90 gradient the diol peak eluted at 10.12 min. LC-MS: $C_{20}H_{27}NO_4$ $[M+H]^+$: 346.24. The $^1H$ NMR spectrum of 6 is shown in FIGS. 5A-5B.

Figure 6:
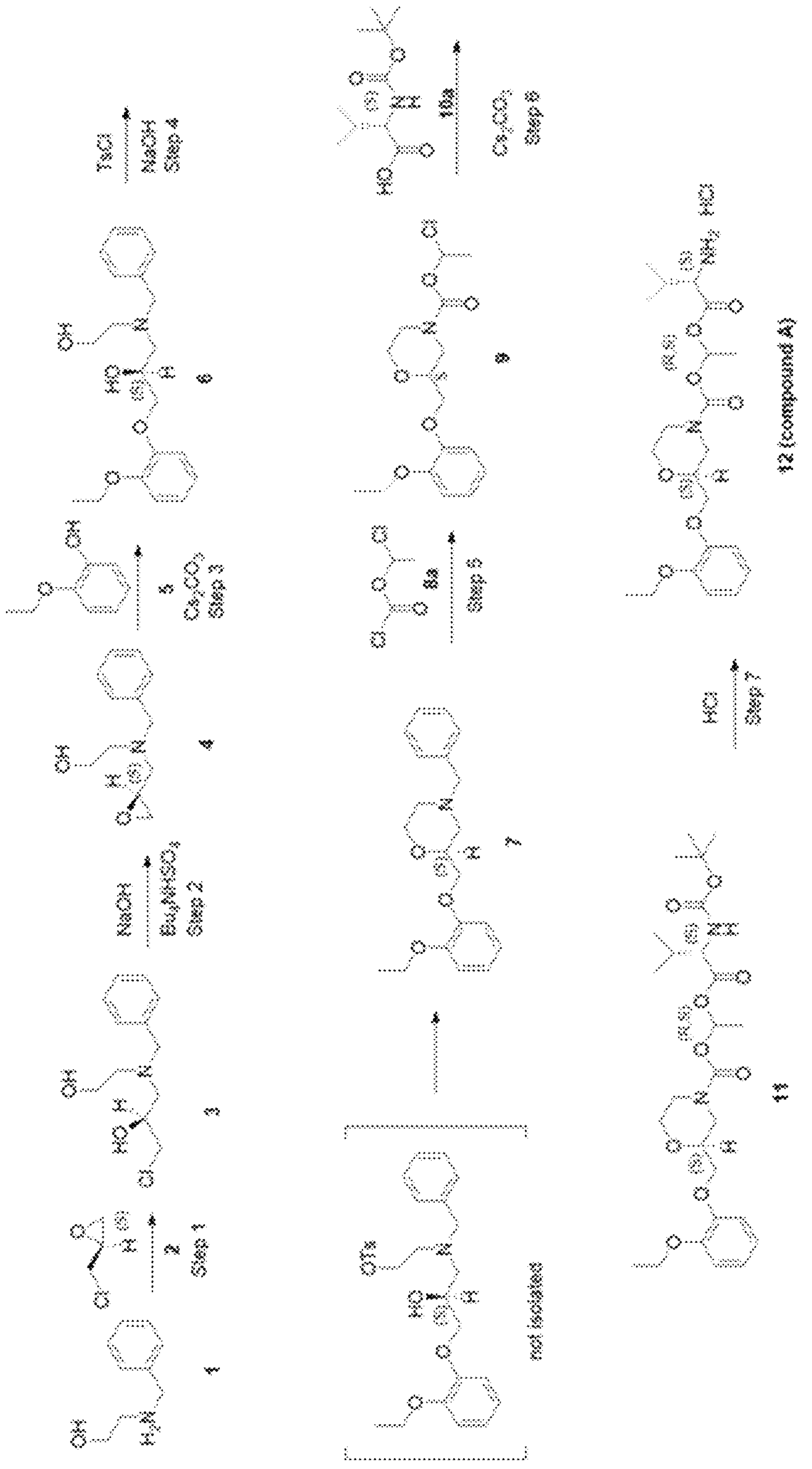
FIG. 6 shows the synthetic method to prepare compound 12 (compound A) from Example 8.

Step 4: The diol 6 (149 g) was dissolved in 400 ml of toluene and 4.92 g of benzyl triethylammonium chloride (22 mmol) was added. Under mechanical stirring, 103.65 g of sodium hydroxide beads (2.6 mol) was added. The temperature increased to 30° C. and was stirred at room temperature for 30 min. The mixture was then cooled in an ice bath to 20° C. and p-toluenesulfonyl chloride (82.3 g, 430 mmol) was added in portions over 1 hr with ice bath cooling to keep the internal temperature at 25±2° C., then stirred at room temperature for 1.5 hr. The mixture was poured into 500 ml of cold water, stirred for 20 min and the layers were separated. The aqueous phase was extracted with toluene 3×150 ml and the extracts washed with 2N NaOH, 6×150 ml, brine (2×), and dried over magnesium sulfate. The toluene was removed on a rotary evaporator to give 160 g of the (S)-4-benzyl-2-((2-ethoxyphenoxy)methyl)morpholine 7 as a yellow oil. The crude product (free base) was shown by chiral SFC to be ca. 80% (S). LC-MS: $C_{20}H_{25}NO_3$ $[M+H]^+$: 328.28. The $^1H$ NMR spectrum of 6 is shown in FIGS. 6A-6B.

(S)-4-benzyl-2-((2-ethoxyphenoxy)methyl)morpholine (160 g) was dissolved in 130 ml of ethyl acetate and the solution cooled in an ice bath. To the solution was added 130 ml of 4N HCl in dioxane and the solution was stirred for 20 min then the solvent was evaporated on a rotary evaporator giving 207 g of the salt 7 HCl as an orange oil. To the crude salt was added 40 ml of ethanol and the mixture was warmed to dissolve then 100 ml of ethyl acetate was added followed by 7.8 ml of water. The solution was seeded with the crystalline HCl salt of 99+% (S) configuration and placed in a freezer at −15° C. over the weekend. The white crystalline product was filtered off and washed with 1:3 ethanol:ethyl acetate and air dried to give 47.23 g of (S)-4-benzyl-2-((2-ethoxyphenoxy)methyl)morpholine HCl (7 HCl) having 99.5% S configuration by chiral SFC analysis. The mother liquor was essentially racemic (49:51) and was discarded.

A subsequent run of the previous reaction (from 600 mmol of 1) gave 48.87 g of 7·HCl that was recrystallized to give 47.09 g of 7·HCl. A subsequent run of the previous reaction (170 mmol of 1) gave 14.6 g of 7·HCl.

The total yield of 108.92 g of (S)-4-benzyl-2-((2-ethoxyphenoxy)methyl)morpholine HCl (7) obtained starting from a total of 1.37 mol of 1 is 21.8%. There were no chromatographic purifications required and the product is >99% the (S)-enantiomer.

Conversion of to (S)-4-benzyl-2-((2-ethoxyphenoxy) methyl)morpholine HCl to 1-[(S)-2-Amino-3-methylbutyroxy]ethyl (S)-2-[(o-ethoxyphenoxy)methyl]-4-morpholinecarboxylate HCl The key intermediate in the synthesis of 1-[(S)-2-Amino-3-methylbutyroxy]ethyl (S)-2-[(o-ethoxyphenoxy)methyl]-4-morpholinecarboxylate HCl (12) from (S)-2-((2-ethoxyphenoxy)methyl)morpholine is the chlorocarbamate (9) initially obtained by reaction of (S)-2-((2-ethoxyphenoxy) methyl)morpholine with 1-chloroethylchloroformate (8). Using (S)-4-benzyl-2-((2-ethoxyphenoxy)methyl)morpholine as a precursor, reaction with 1-chloroethyl chloroformate was designed to generate the NH compound in the course of N-debenzylation (see, Olofson, et al., J. Org. Chem. 1984, 49, 2081-2082; the published procedure used N-ethyl piperidine as the example).

Extrapolating to the synthesis of 1-[(S)-2-Amino-3-methylbutyroxy]ethyl (S)-2-[(o-ethoxyphenoxy)methyl]-4-morpholinecarboxylate HCl (12) and other (S)-2-((2-ethoxyphenoxy)methyl)morpholine prodrugs, the intermediate chlorocarbamate 9 was produced from (S)-4-benzyl-2-((2-ethoxyphenoxy)methyl)morpholine (7) and 1-chloroethyl chloroformate 8 with the loss of benzyl chloride to form 9, bypassing the need to produce and use (S)-2-((2-ethoxyphenoxy)methyl)morpholine in the overall process.

As shown in Scheme VIII, (S)-4-benzyl-2-((2-ethoxyphenoxy)methyl)morpholine (7) was treated with chloroformate 8 giving the N-benzyl-N-carbamoyl salt (not isolated) that eliminated benzyl chloride to form the 1-chloroethyl carbamate 9. The reaction was very rapid even at room temperature with (S)-4-benzyl-2-((2-ethoxyphenoxy)methyl) morpholine. and the carbamate 9 did not convert to 2-((2-ethoxyphenoxy)methyl)morpholine under the conditions. In the initial studies, the crude product was extracted with hexane/acetonitrile solvent extraction to remove the benzyl chloride that is formed in the elimination of benzyl chloride from 9. An improved method (detailed below) was found in which triethylamine was added to the mixture to react with the benzyl chloride byproduct, forming benzyl triethylammonium chloride, a water soluble quaternary salt that could be washed out of the crude product with water.

The synthesis was completed by reacting the chlorocarbamate 9 with N-BOC-1-valine (10) to give the N-BOC-1-valine ester (11). Treatment of 11 with HCl gave 1-((L-valyl) oxy)ethyl (2S)-2-((2-ethoxyphenoxy)methyl)morpholine-4-carboxylate HCl (12). A key observation is that the product 1-[(S)-2-amino-3-methylbutyroxy]ethyl (S)-2-[(o-ethoxyphenoxy)methyl]-4-morpholinecarboxylate HCl (12) can be extracted from aqueous HCl solution into dichloromethane, without carrying over any byproducts.

(S)-4-benzyl-2-((2-ethoxyphenoxy)methyl)morpholine HCl (36.3 g, 100 mmol) was stirred with 200 ml of 2N NaOH and 160 ml of water for 1 hr at ca. 16° C. then extracted with 1×400 ml and 1×200 ml of dichloromethane. The solvent was evaporated to give 32.7 g of (S)-4-benzyl-2-((2-ethoxyphenoxy)methyl)morpholine free base.

Experimental Details

Step 5: A solution of (S)-4-benzyl-2-((2-ethoxyphenoxy) methyl)morpholine free base (32.7 g, 100 mmol) in 150 ml of dichloromethane was cooled in an ice-water bath. To the solution was added a solution of 1-chloroethylchloroformate (8, 18.57 g, 130 mmol) in 50 ml of dichloromethane over 30 min with ice-bath cooling and the solution was stirred for 2 hr under $N_2$ then warmed to room temperature and stirred an additional 1 hr. To remove the benzyl chloride byproduct, triethylamine (30.3 g, 300 mol) in 25 ml of dichloromethane was added slowly over 30 min at room temperature, stirred for a total of 72 hr, then washed with 150 ml of water, 150 ml of 1N HCl, 150 ml of bicarbonate, 100 ml of brine, dried over $Na_2SO_4$, decolorized with Norit A, filtered through Celite and evaporated to give 35 g of the chlorocarbamate (9). LC-MS: $C_{16}H_{22}ClNO_5Na$ $[M+Na]^+$: 366.12.

Step 6: N-Boc-L-valine (34.32 g, 160 mmol) was dissolved in 125 ml of DMF and cesium carbonate (26 g, 80 mmol) was added in portions. The mixture was stirred for 30 min at room temperature then the crude chlorocarbamate 9 (35 g) in 75 ml of DMF was added at room temperature then the mixture was stirred at 85° C. for 1 hr then allowed to cool to room temperature. Ethyl acetate (250 ml was added and the solution washed with 2×150 ml of water, 1×125 ml of bicarbonate, 2×250 ml of 1N HCl and 1×125 ml of brine, dried over $Na_2SO_4$ and evaporated to give 55 g of crude 1-[(S)-2-(tert-Butoxycarbonylamino)-3-methylbutyroxy] ethyl (S)-2-[(o-ethoxyphenoxy)methyl]-4-morpholinecarboxylate (11). LC-MS: $C_{26}H_{40}N_2O_9Na$ $[M+Na]^+$: 547.14.

The above process was repeated at 1.74× scale starting from 63.16 g (S)-4-benzyl-2-((2-ethoxyphenoxy)methyl) morpholine HCl (174 mmol) to give an additional 91 g of 1-[(S)-2-(tert-Butoxycarbonylamino)-3-methylbutyroxy] ethyl (S)-2-[(o-ethoxyphenoxy)methyl]-4-morpholinecarboxylate (11).

Figure 7:
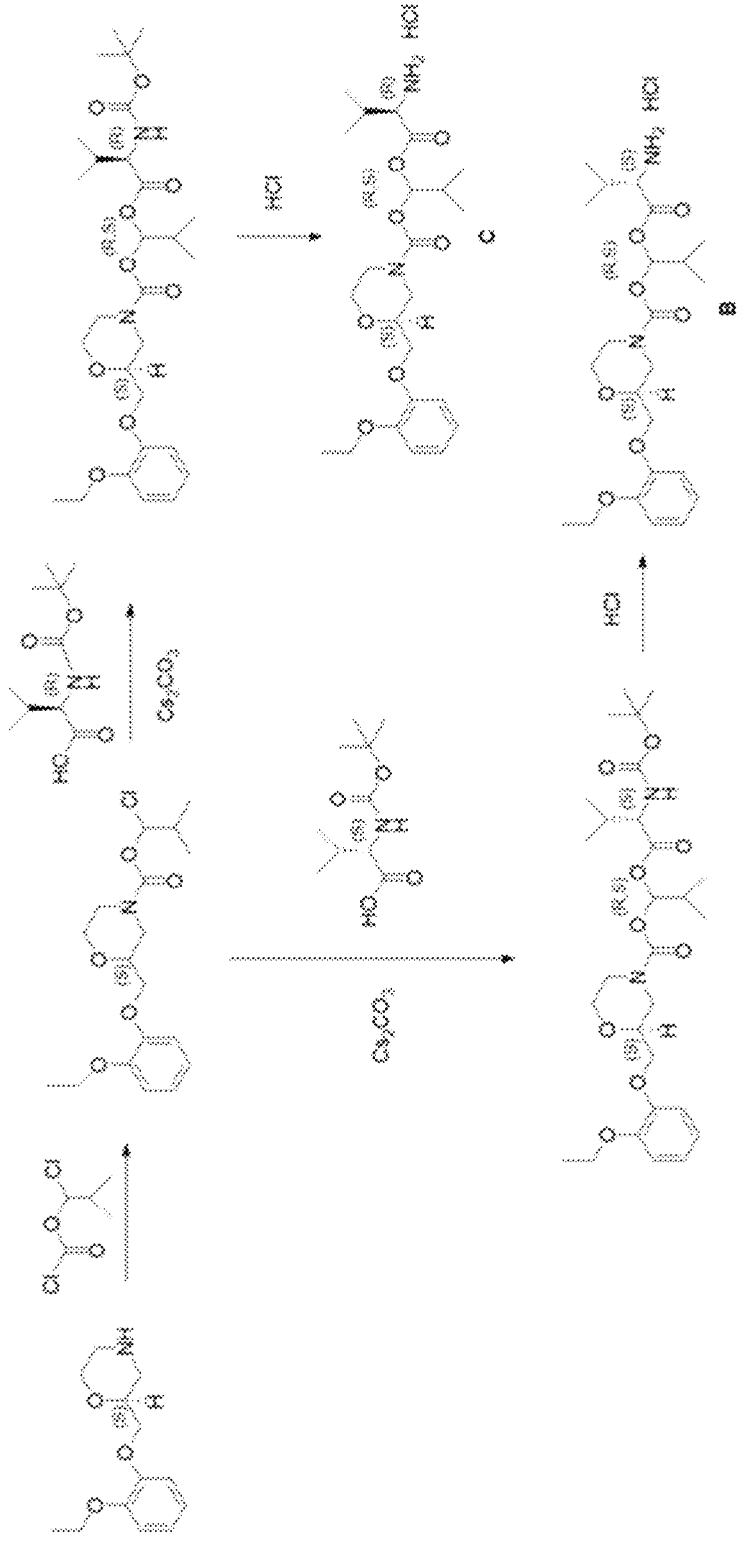
FIG. 7 shows the synthetic method to prepare compounds B and C.

Step 7: The 55 g of the crude 1-[(S)-2-(tert-Butoxycarbonylamino)-3-methylbutyroxy]ethyl (S)-2-[(o-ethoxyphenoxy)methyl]-4-morpholinecarboxylate (11) (100 mmol) was dissolved in 100 ml of ethyl acetate and 100 ml of 4N HCl in dioxane was added. The solution was stirred at room temperature for 4 hr then concentrated under vacuum. The crude HCl salt 1-[(S)-2-Amino-3-methylbutyroxy]ethyl (S)-2-[(o-ethoxyphenoxy)methyl]-4-morpholinecarboxylate HCl (56 g) was dissolved in 300 ml of ethyl acetate and extracted with 2×300 ml of 1N HCl. The combined HCl layer was washed with 200 ml of 50% ethyl acetate in hexane then extracted with 600 ml of dichloromethane. The dichloromethane layer was dried over $Na_2SO_4$ and evaporated to give 40 g of 1-[(S)-2-Amino-3-methylbutyroxy] ethyl (S)-2-[(o-ethoxyphenoxy)methyl]-4-morpholinecarboxylate·HCl (12). LC-MS: $C_{21}H_{32}N_2O_7$ $[M+H]^+$: 425.29. The $^1H$ NMR spectrum of 12 is shown in FIGS. 7A-7B.

In a subsequent run, 1-[(S)-2-(tert-Butoxycarbonylamino)-3-methylbutyroxy]ethyl (S)-2-[(o-ethoxyphenoxy)methyl]-4-morpholinecarboxylate (11) (91 g) was treated with 4N HCl in dioxane as above to give 62 g of 1-[(S)-2-Amino-3-methylbutyroxy]ethyl (S)-2-[(o-ethoxyphenoxy)methyl]-4-morpholinecarboxylate HCl (12). An additional 3.5 g was obtained from the dichloromethane (emulsion standing overnight to separate). This was lyophilized separately.

Multiple lots of 1-[(S)-2-Amino-3-methylbutyroxy]ethyl (S)-2-[(o-ethoxyphenoxy)methyl]-4-morpholinecarboxylate HCl (12, 18 g, 40 g, and 62 g) were combined (total of 120 g) and dissolved in 200 ml of acetonitrile and 400 ml of water. The solution was decolorized with Norit and filtered through Celite then lyophilized to give a total of 112.92 g of the product 1-[(S)-2-Amino-3-methylbutyroxy]ethyl (S)-2-[(o-ethoxyphenoxy)methyl]-4-morpholinecarboxylate (12) as the HCl salt as an off-white solid. HPLC indicated the product was 98.5% pure. Rinsings of the lyophilization flasks were re-lyophilized to give an additional 6 g.

The total yield of 1-[(S)-2-Amino-3-methylbutyroxy] ethyl (S)-2-[(o-ethoxyphenoxy)methyl]-4-morpholinecarboxylate HCl (12, 112.92+3.5+6=122.42 g) represents an overall yield from (S)-4-benzyl-2-((2-ethoxyphenoxy) methyl)morpholine HCl of 81.97%.

While this description is made with reference to exemplary embodiments, it will be understood by those skilled in the art that various changes may be made and equivalents may be substituted for elements thereof without departing from the scope. In addition, many modifications may be made to adapt a particular situation or material to the teachings hereof without departing from the essential scope. Also, in the drawings and the description, there have been disclosed exemplary embodiments and, although specific terms may have been employed, they are unless otherwise stated used in a generic and descriptive sense only and not for purposes of limitation, the scope of the claims therefore not being so limited. Moreover, one skilled in the art will appreciate that certain steps of the methods discussed herein may be sequenced in alternative order or steps may be combined. Therefore, it is intended that the appended claims not be limited to the particular embodiment disclosed herein.

The invention claimed is:

1. A compound of the following formula:

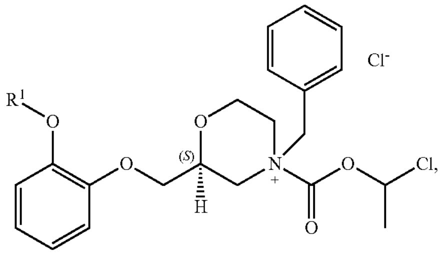

wherein $R^1$ is $C_1$-$C_6$ alkyl, aryl, heteroaryl, or heterocycloalkyl.

2. A compound of claim 1, wherein $R^1$ is $C_1$-$C_6$ alkyl.

3. A compound of claim 1, wherein $R^1$ is $CH_2CH_3$.

4. A compound of claim 1, wherein $R^1$ is $CH_3$.

5. A compound of the following formula:

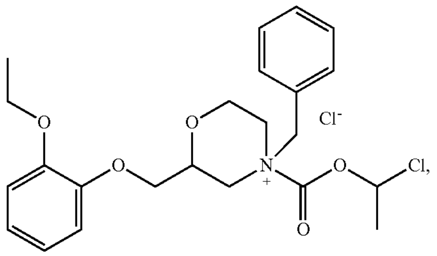

6. A compound of the following formula:

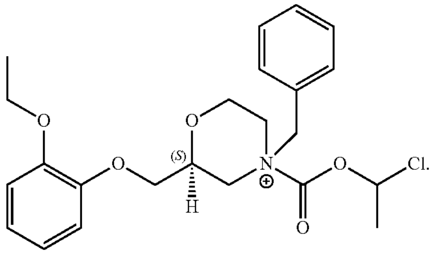

* * * * *